US011255834B2

(12) United States Patent
Musho et al.

(10) Patent No.: US 11,255,834 B2
(45) Date of Patent: Feb. 22, 2022

(54) PHYSICAL CHARACTERISTIC DETERMINATION OF A BIOLOGICAL SAMPLE

(71) Applicant: Conductive Technologies, Inc., York, PA (US)

(72) Inventors: Matthew K. Musho, York, PA (US); Christina A. Beaverson, York, PA (US); Nicholas F. Szabo, York, PA (US)

(73) Assignee: Conductive Technologies, Inc., York, PA (US)

( * ) Notice: Subject to any disclaimer, the term of this patent is extended or adjusted under 35 U.S.C. 154(b) by 179 days.

(21) Appl. No.: 15/465,176

(22) Filed: Mar. 21, 2017

(65) Prior Publication Data

US 2017/0285016 A1 Oct. 5, 2017

Related U.S. Application Data

(60) Provisional application No. 62/311,587, filed on Mar. 22, 2016.

(51) Int. Cl.
*G01N 27/327* (2006.01)
*G01N 33/15* (2006.01)
*G01N 33/00* (2006.01)

(52) U.S. Cl.
CPC ......... *G01N 33/15* (2013.01); *G01N 27/3272* (2013.01); *G01N 27/3274* (2013.01); *G01N 33/00* (2013.01)

(58) Field of Classification Search
CPC ............... G01N 27/327–3272; G01N 27/3274
See application file for complete search history.

(56) References Cited

U.S. PATENT DOCUMENTS 5,120,420 A * 6/1992 Nankai ............... C12Q 1/001
204/403.11
5,565,143 A * 10/1996 Chan ..................... H01B 1/20
252/514

(Continued)

FOREIGN PATENT DOCUMENTS

JP WO 2015/079635 A1 * 6/2015 ............ C12Q 1/006

OTHER PUBLICATIONS

Joshi (Evaluation of Silver/Graphite Ink Blends for use in Printed Electronics, Master's thesis, Apr. 2011, the relevant pages is provided with this office action, the full text is available at Joshi: https://scholarworks.wmich.edu/masters_theses/639/) (Year: 2011).*

(Continued)

*Primary Examiner* — Alexander S Noguerola
(74) *Attorney, Agent, or Firm* — Blanchard & Associates

(57) ABSTRACT

Test sensors, methods, and systems are described that include a first electrode pair having either two active electrodes or an inactive working electrode paired with an active counter electrode. These active electrodes are different than having an electron transfer mediator on an inactive electrode because in addition to the structural differences between an electrode directly in contact with the conductors of the test sensor verses a reagent coating, there are chemical and functional differences. The active electrodes are formed from an electrode core material including an element that loses or acquires electrons during the analysis and directly participates in the electrochemical reaction of the sample. As the active electrodes are insoluble in the sample during the analysis, an electrochemically stable potential is provided by the active electrodes that can reliably operate at higher operating potentials than conventional electron transfer mediator reagents coated on an inactive electrode.

73 Claims, 8 Drawing Sheets

(56) References Cited

U.S. PATENT DOCUMENTS

| | | |
|---|---|---|
| 7,955,492 B2 | 6/2011 | Fujiwara et al. |
| 7,966,859 B2 | 6/2011 | Wu et al. |
| 8,007,656 B2 | 8/2011 | Wu et al. |
| 8,480,869 B2 | 7/2013 | Fujiwara et al. |
| 8,535,497 B2 | 9/2013 | Fujiwara et al. |
| 8,540,864 B2 | 9/2013 | Fujiwara et al. |
| 8,691,072 B2 | 4/2014 | Fujiwara et al. |
| 10,066,253 B2* | 9/2018 | Fujiwara .............. C12Q 1/006 |
| 10,174,211 B2* | 1/2019 | Brown .................. C03C 8/04 |
| 2007/0045126 A1* | 3/2007 | Beer .................. G01N 27/3272 205/777.5 |
| 2007/0202606 A1* | 8/2007 | Noble ................ G01N 27/3274 436/164 |
| 2008/0173552 A1* | 7/2008 | Wu .................... G01N 27/3273 205/775 |
| 2010/0267161 A1* | 10/2010 | Wu ...................... C12Q 1/001 436/149 |
| 2010/0276303 A1 | 11/2010 | Fujiwara et al. |
| 2011/0139634 A1 | 6/2011 | Chou et al. |
| 2016/0273017 A1* | 9/2016 | Fujiwara .............. C12Q 1/006 |

OTHER PUBLICATIONS

Dupont Biomedical Sensor Materials Product Selector Guide (Year: 2013).*
Jen et al., "Transcriptional response of Lymphoblastoid Cells to Ionizing Radiation," Genome Res., 2003 13: 2092-2100 (Year: 2003).*
Achel et al., "Radioprotective and Antimutagenic Effects of Pycnanthus angolensis Warb Seed Extract against Damage Induced by X rays," J. Clin. Med. 2020, 9, 6 (Year: 2020).*
Kozo Hirokawa, An enzymatic method for the determination of hemoglobinA1C, Biotechnology Letters 2005 27: 963-968.

* cited by examiner

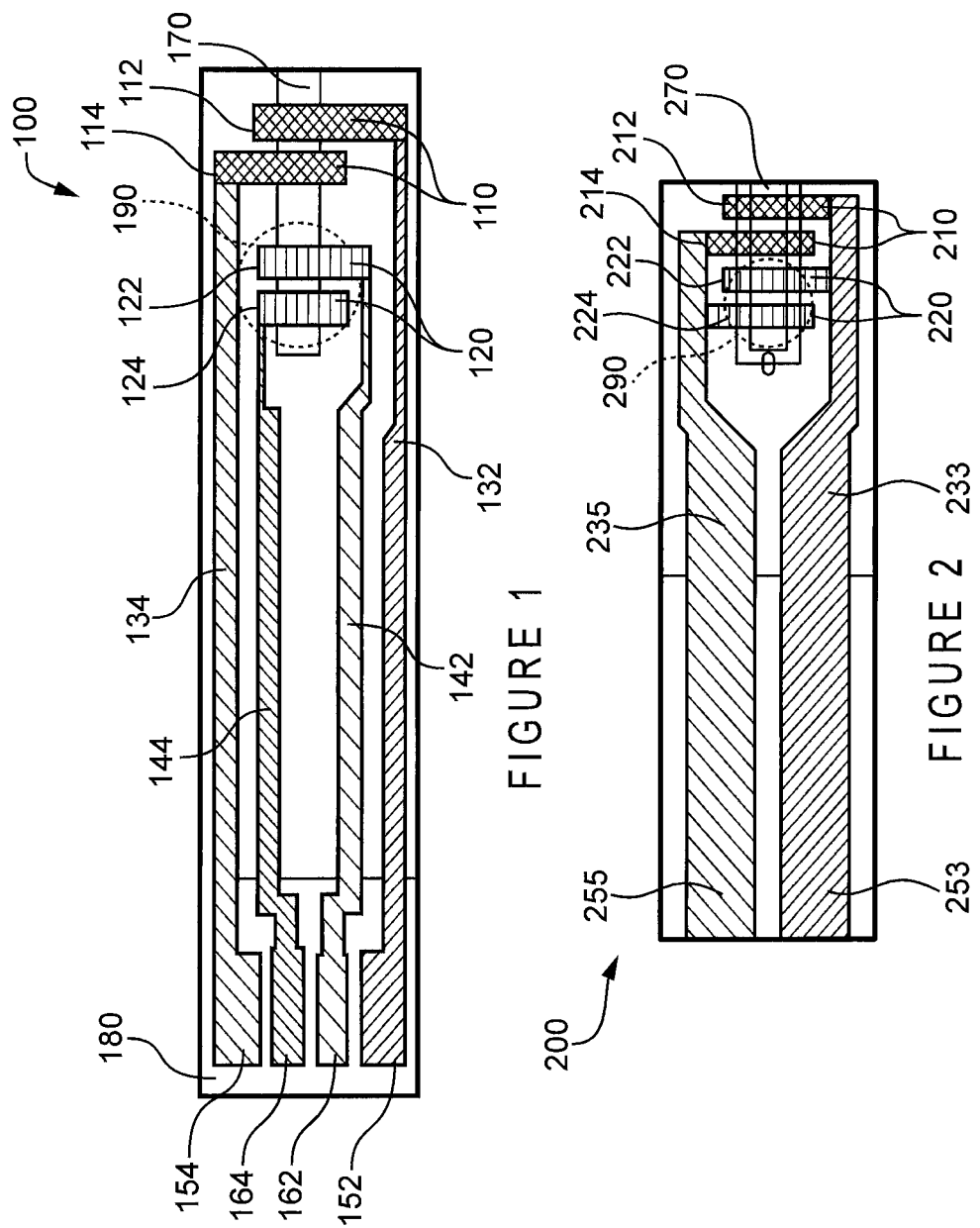

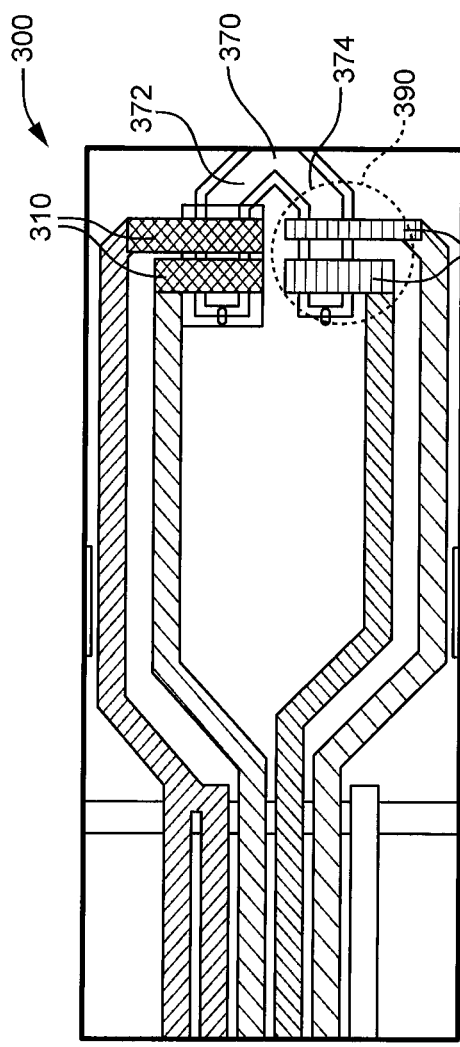
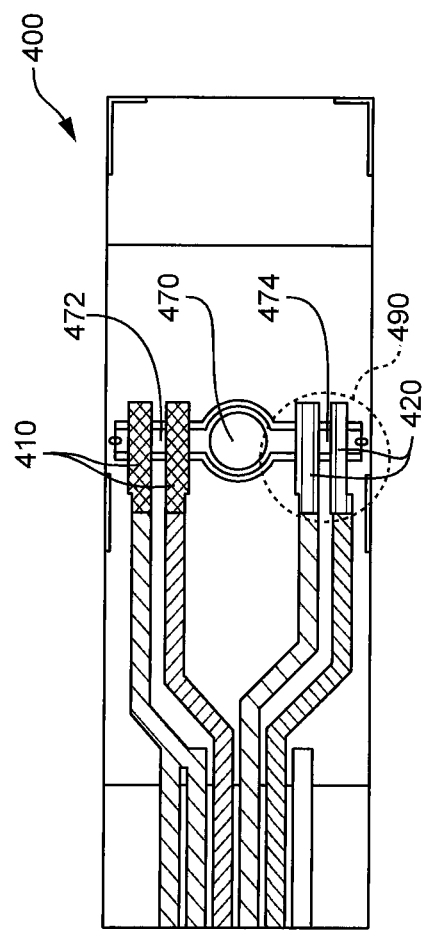
FIGURE 3
FIGURE 4

PHYSICAL CHARACTERISTIC DETERMINATION OF A BIOLOGICAL SAMPLE

REFERENCE TO RELATED APPLICATIONS

This application claims the benefit of U.S. Provisional Application No. 62/311,587 entitled "Physical Characteristic Determination of a Biological Sample" filed Mar. 22, 2016, which is incorporated by reference in its entirety.

BACKGROUND

Electrochemical biosensor systems provide an analysis of one or more constituents of blood samples. The biosensor systems include a measurement device having electrical conductor contacts that connect with electrical conductors of the test sensor. The electrical conductors of the test sensor are made from conductive materials, such as solid metals, metal pastes, conductive carbon, conductive carbon pastes, conductive polymers, and the like. The electrical conductors of the test sensor typically connect to working, counter, reference, and/or other electrodes that extend into a sample reservoir. One or more electrical conductors also may extend into the sample reservoir to provide functionality not provided by the electrodes.

A blood sample is introduced into the sample reservoir of the test sensor for analysis. During the analysis, the test sensor includes at least two electrodes in contact with the blood sample referred to as the working electrode and the counter electrode. The sample completes an electrical circuit (allows electrons to flow) between the working and counter electrodes of the test sensor. The test sensor may include additional electrodes or electrical conductors in contact with the blood sample within the sample reservoir that provide a known potential during the analysis (often referred to as a reference or pseudo-reference electrode), sense the presence of the blood sample, and the like. If the counter electrode is active, it may provide a known potential during the analysis.

The blood sample may be drawn from the body of an animal or may be a derivative of such sample, including an extract, a dilution, a filtrate, or a reconstituted precipitate. The analysis performed by the biosensor system of the blood sample determines the content of hematocrit in the blood sample and may determine the presence and/or concentration of one or more analytes, such as alcohol, glucose, uric acid, lactate, cholesterol, bilirubin, ketones, or phenylalanine through the use of an analyte specific ionizing agent.

The measurement device applies an electrical input through the electrical conductor contacts to the electrical conductors of the test sensor. The electrical conductors convey the input through the electrodes into the blood sample present in the sample reservoir. The electrical input may be a potential or current and may be constant, variable, or a combination thereof such as when an AC input is applied with a DC offset. The input may be applied as a single pulse or in multiple pulses, sequences, or cycles.

The oxidation/reduction or redox reaction of one or more constituents of the blood sample generates an electrical output in response to the electrical input. The measurement device measures the electrical output from the test sensor as a current (as generated by amperometry or voltammetry), as a potential (as generated by potentiometry), or as an accumulated charge (as generated by coulometry).

The analyte concentration of the blood sample is determined from an analyte responsive electrical output generated by the redox reaction of the analyte or a species responsive to the concentration of the analyte when the electrical input is applied to the sample. An analyte specific ionizing agent may be added to the sample to enhance electron transfer from the analyte to a second species during the redox reaction. The analyte specific ionizing agent reacts with a single analyte or substantially with a single analyte to provide specificity to a portion of the generated output. An electron transfer mediator may be used to maintain the oxidation state of the analyte specific ionizing agent and more effectively transfer electrons to the working electrode of the test sensor. The measurement device may have the processing capability to measure and correlate the electrical output measured from the test sensor with the presence and/or concentration of one or more analytes in the biological fluid.

While not wishing to be bound by any particular theory, in conventional biosensors for determining blood glucose concentrations for example, glucose may be oxidized by an enzyme, which then transfers the electron to a mediator. This chemically reduced mediator then travels to the working electrode where the chemically reduced mediator is electrochemically oxidized by the potential applied across the working and counter electrode conductors of the test sensor. The oxidized mediator may then return to the reduced enzyme to be re-oxidized to continue the electrochemical reaction of the sample. The amount of mediator being oxidized or reduced by the enzyme and traveling to the working electrode may be correlated to the current flowing between the working and counter electrodes of the test sensor. This current is responsive to the analyte concentration of the sample as the current flowing between the working and counter electrodes is responsive to the reaction of the analyte with the analyte-specific enzyme.

For the quantitative analysis of an analyte in the sample, such as glucose, the electrical output measured at the working electrode should be directly proportional to the diffusion coefficient of the charged analyte or a charged species responsive to the analyte, such as the electron transfer mediator. However, the "hematocrit effect" interferes with this process because the red blood cells in the blood sample (hematocrit or "Hct") block the diffusion of the charged analyte or the charged species responsive to the analyte to the working electrode of the test sensor. In this way, the hematocrit effect influences the amount of electrical output (e.g. current) measured at the working electrode without any correlation to the amount of analyte (e.g. glucose) in the sample. Thus, for amperometric and voltammetric analysis methods, the current measured by the measurement device at the working electrode of the test sensor varies not only with the analyte concentration of the blood sample, but with the Hct content of the blood sample. As the red blood cells physically interfere with the diffusion of the charged analyte or species responsive to the analyte to the working electrode of the test sensor, the red blood cells may be considered a physical interferent to the analysis of the analyte in the blood sample.

The Hct content of a blood sample varies according to the condition of the animal from which the blood sample is drawn. In humans, the Hct content is normally 39% to 50% by volume (volume of red blood cells/total volume of blood sample*100%) for adult males and 36% to 45% by volume for adult females. Thus, it is desirable to know the Hct content of a blood sample being quantitatively analyzed for an analyte, such as glucose, so that the determined analyte concentration of the blood sample may be corrected based on the Hct content of the blood sample. The Hct content of a blood sample also may be used independently of analyte quantification, such as when blood viscosity or anemia is of interest.

While not wishing to be bound by any particular theory, unlike for an analyte, red blood cells are not believed to undergo a redox reaction during biosensor analysis. Thus, to determine electrochemically the Hct content of a blood sample, a species that can undergo an electrochemical redox reaction at a working electrode is needed. However, to the extent possible, the concentration of this species in the blood sample should not be responsive to that of the analyte concentration of the sample, as different blood samples have different analyte concentrations. Other challenges of Hct analysis include (1) to obtain a Hct responsive output that is large in relation to the non-Hct responsive background output and (2) to obtain a Hct responsive output that provides Hct responsive output amplitudes that are measurably different at different Hct blood sample contents—in combination, the detection sensitivity of the Hct analysis. For example, if the amplitude of the Hct output only changes by 10% or less from 39% to 50% Hct blood sample content, the accuracy of the determined Hct sample content will be poor as there is not enough change in the amplitude of the Hct output to differentiate the different Hct sample contents.

The problem of accurately determining the Hct sample content from small changes in output amplitude is described in U.S. Pat. No. 8,691,072 ('072 patent) where the problem of an only 8% change in output amplitude in relation to a 20% change in Hct sample content is described. Test sensors having this lack of Hct sensitivity issue are described in International Publications 2005/054839 (U.S. Pat. No. 8,088,271) and 2005054840 (U.S. Pat. No. 8,535,497) according to the authors of the '072 patent. The authors of the '072 patent addressed this lack of output amplitude (detection sensitivity) by placing a reductant (ferrocyanide) at the working electrode and an oxidant or reducible species (ferricyanide) at the counter electrode. Thus, different species of a redox pair are present at the working and the counter electrodes of the test sensor. The design of the '072 patent having a reductant at the working electrode and an oxidant at the counter electrode was an improvement over the older '497 patent, where the oxidant ferricyanide was only at or in the vicinity of the counter electrode (so it could be solubilized at the counter electrode)—thus not present at the working electrode. In these systems, a current flow resulted from the test sensor that is inversely proportional to the Hct content of the sample.

In conventional test sensors, electrical conductors transfer electricity from the contacts of the measurement device to the electrodes. Generally, an electrode material or "core" is applied to a portion of the surface of the electrical conductors of the test sensor to form the electrodes of the test sensor by screen printing, sputtering, vapor-deposition, or similar method. The working electrode core material may be palladium, platinum, gold, titanium, carbon, or a mixture of these, for example, which does not undergo oxidation at the potential and duration at which the analysis is performed. A polymer may be added to the electrode core material or used as a film on the core material to seal the electrode core material from the sample. In some instances, the electrode core includes layers of different core materials. The counter electrode is generally formed similarly to the working electrode and may have a single or multiple layers of different core material on the surface of the electrical conductor. The redox species is then applied only to the counter electrode as in the '497 patent or to both the counter and working electrodes as in the '072 patent. Electrodes of this type are inactive.

The 2011/0139634 U.S. Pat. Pub. ('634 publication) to Chou takes a different approach. The '634 publication uses a dedicated reaction zone and a pair of inactive electrodes (silver conductors rendered inactive by a carbon cover to form the electrodes in the reaction zone) to directly measure the Hct content of the sample with an AC electrical input having a DC offset. Thus, a redox species that participates in the electrochemical analysis of the sample is not present. As a DC input will not provide a useful Hct output with inactive electrodes, an AC input is used for Hct determination and the positive correlation between the Hct content of the sample and impedance may be used to determine the Hct content of the sample.

As can be seen from the above description, there is an ongoing need for simple and efficient materials and methods for determining the Hct content of blood samples through electrochemical analysis. The test sensors, electrodes, and methods of the present invention overcome at least one of the disadvantages associated with conventional test sensors and methods.

SUMMARY

In one aspect, the invention provides a test sensor for determining a corrected analyte concentration of a sample including a substrate; at least two electrical conductor contacts and at least two electrical conductors, each electrical conductor contact in electrical communication with an electrical conductor, where the electrical conductor contacts are on the substrate; a lid on the substrate forming a sample reservoir with the substrate, the sample reservoir comprising an inlet port; and at least two pair of electrodes in the sample reservoir in electrical communication with the electrical conductors, where a first electrode pair in the sample reservoir includes an active counter electrode, and a second electrode pair in the sample reservoir includes an analyte specific ionizing agent on a working electrode of the second electrode pair.

In another aspect of the invention, there is a test sensor for determining a physical characteristic of a sample, including a substrate; two electrical conductor contacts and two electrical conductors, each electrical conductor contact in electrical communication with an electrical conductor, where the electrical conductor contacts are on the substrate; a lid on the substrate forming a sample reservoir with the substrate, the sample reservoir comprising an inlet port; and one pair of electrodes in the sample reservoir and in electrical communication with the electrical conductors, where the one pair of electrodes in the sample reservoir includes an active counter electrode.

In another aspect of the invention, there is a method for determining a corrected analyte concentration of a sample including applying a potential of at least 400 mV to a pair of electrical conductor contacts in electrical communication with a pair of electrical conductors in electrical communication with a first electrode pair; generating an electrical output from a second electrode pair responsive to an analyte concentration of a sample, the sample in electrical communication with the second electrode pair; generating an electrical output from a first electrode pair responsive to a physical characteristic of the sample, the sample in electrical communication with the first electrode pair, the first electrode pair including an active counter electrode; correcting the electrical output from the second electrode pair with the electrical output from the first electrode pair; and determining a corrected analyte concentration of the sample. The correcting my include determining an uncorrected analyte concentration of the sample and a physical characteristic content of the sample with previously prepared calibration curves, the previously prepared calibration curves including a relationship between analyte responsive generated output from the second electrode pair and analyte concentration of the sample, and a relationship between physical characteristic generated output from the first electrode pair and physical characteristic content of the sample; and correcting the uncorrected analyte concentration of the sample with the physical characteristic content of the sample.

In another aspect of the invention, there is a method for determining a physical characteristic content of a sample, including applying a potential from 2,000 mV to 6,000 mV to two electrical conductor contacts and two electrical conductors, each electrical conductor contact in electrical communication with an electrical conductor; generating an electrical output from one electrode pair responsive to a physical characteristic of the sample, the sample in electrical communication with the one electrode pair, the one electrode pair including an active counter electrode; and determining a physical characteristic content of the sample from the electrical output.

In another aspect of the invention, there is a system for determining a corrected analyte concentration of a sample including a measurement device having contacts in electrical communication with electrical conductor contacts of a test sensor, each electrical conductor contact in electrical communication with an electrical conductor, where the electrical conductor contacts are on a substrate of the test sensor, the measurement device includes contacts in electrical communication with circuitry including a processor in electrical communication with an electrical input generator and with a storage medium, the test sensor includes a lid on the substrate forming a sample reservoir with the substrate, the sample reservoir comprising an inlet port, the test sensor includes at least two pair of electrodes in the sample reservoir in electrical communication with the electrical conductors of the test sensor, where a first electrode pair in the sample reservoir includes an active counter electrode, and a second electrode pair in the sample reservoir includes an analyte specific ionizing agent on a working electrode of the second electrode pair; the electrical input generator is configured to apply an electrical input of at least 400 mV to the contacts of the measurement device in response to an instruction from the processor; the test sensor is configured to generate an electrical output from the second electrode pair responsive to an analyte concentration of a sample, the sample in electrical communication with the second electrode pair; the test sensor is configured to generate an electrical output from the first electrode pair responsive to a physical characteristic of the sample, the sample in electrical communication with the first electrode pair, the first electrode pair including an active counter electrode; the processor is configured to correct the electrical output from the second electrode pair with the electrical output from the first electrode pair in response to non-transient instructions stored in the storage medium; and the processor is configured to determine a corrected analyte concentration of the sample in response to non-transient instructions stored in the storage medium.

In another aspect of the invention, there is a system for determining a physical characteristic of a sample, including a measurement device having contacts in electrical communication with electrical conductor contacts of a test sensor, each electrical conductor contact in electrical communication with an electrical conductor, where the electrical conductor contacts are on a substrate of the test sensor, the measurement device includes contacts in electrical communication with circuitry including a processor in electrical communication with an electrical input generator and with a storage medium, the test sensor includes a lid on the substrate forming a sample reservoir with the substrate, the sample reservoir comprising an inlet port, the test sensor includes one pair of electrodes in the sample reservoir in electrical communication with the electrical conductors of the test sensor, where the one pair of electrodes in the sample reservoir include an active counter electrode, and the electrical input generator is configured to apply an electrical input from 2,000 mV to 6,000 mV to the contacts of the measurement device in response to an instruction from the processor; the test sensor is configured to generate an electrical output from one electrode pair on the substrate responsive to a physical characteristic of the sample, the sample in electrical communication with the one electrode pair, the one electrode pair including an active counter electrode; the processor is configured to determine a physical characteristic content of the sample in response to non-transient instructions stored in the storage medium.

In another aspect of the invention, there is an active electrode pair for participating in the electrochemical reaction of an analyte in a sample, the active electrode pair including a working electrode, the working electrode consisting essentially of carbon and silver metal, silver metal and silver chloride, and combinations thereof; and a counter electrode, the counter electrode consisting essentially of carbon and silver metal, silver metal and silver chloride, and combinations thereof, where the silver content of the counter electrode is from 70% to 90% (weight/weight).

Other systems, methods, features and advantages of the invention will be, or will become, apparent to one with skill in the art upon examination of the following figures and detailed description. It is intended that all such additional systems, methods, features, and advantages be included within this description, be within the scope of the invention, and be protected by the claims that follow.

BRIEF DESCRIPTION OF THE DRAWINGS

The invention can be better understood with reference to the following drawings and description. The components in the figures are not necessarily to scale, emphasis instead being placed upon illustrating the principles of the invention.

FIG. 1 represents a test sensor having at least four electrodes, with a first working and counter electrode pair for analyzing a physical characteristic, such the Hct content, of the sample and a second working and counter electrode pair for analyzing an analyte in the sample.

FIG. 2 represents a test sensor having at least four electrodes, with a first working and counter electrode pair for analyzing a physical characteristic, such the Hct content, of the sample and a second working and counter electrode pair for analyzing an analyte in the sample.

FIG. 3 represents a test sensor having at least four electrodes, with a first working and counter electrode pair for analyzing the Hct content of the sample and a second working and counter electrode pair for analyzing an analyte in the sample.

FIG. 4 represents a test sensor having at least four electrodes, with a first working and counter electrode pair for analyzing the Hct content of the sample and a second working and counter electrode pair for analyzing an analyte in the sample.

DETAILED DESCRIPTION

Figure 5:
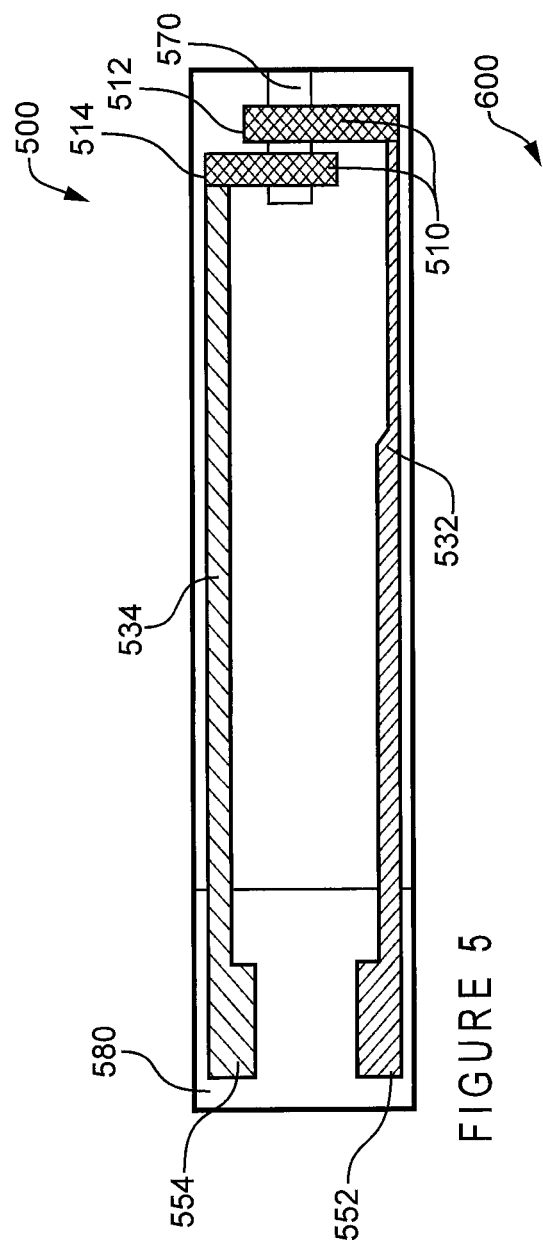
FIG. 5 represents a test sensor having at least two electrodes, with a first working and counter electrode pair for analyzing a physical characteristic, such as the Hct content, of the sample.

Test sensors are described that include a first electrode pair having either two active electrodes or an inactive working electrode paired with an active counter electrode. These active electrodes are different than having an electron transfer mediator on an inactive electrode because in addition to the structural differences between an electrode directly in contact with the conductors of the test sensor verses a reagent coating, there are chemical and functional differences. The active electrodes are formed from an electrode core material including an element that loses or acquires electrons during the analysis and directly participates in the electrochemical reaction of the sample. Preferably, the electrode core material that forms the active electrodes is substantially homogeneous. As the active electrodes are insoluble in the sample during the analysis, an electrochemically stable potential is provided by the active electrodes that can reliably operate at higher operating potentials than conventional electron transfer mediator reagents coated on an inactive electrode. Thus, the active electrodes are both chemically and functionally different than electron transfer mediator coated electrodes and the higher operating potentials provided by the active electrodes provide the ability to determine physical characteristics of the sample.

As discussed in Chou, non-mediator coated electrodes would be expected to require an AC electrical input to generate an output providing useful Hct response and detection sensitivity. However, the disclosed active electrode pairs or the inactive working electrode paired with an active counter electrode unexpectedly provide useful Hct response and detection sensitivity at DC electrical inputs of approximately 400 mV and greater, depending on the electrode pair used.

FIG. 1 represents a test sensor 100 having at least four electrodes, with a first working and counter electrode pair 110 for analyzing a physical characteristic, such the Hct content, of the sample and a second working and counter electrode pair 120 for analyzing an analyte in the sample. The first electrode pair 110 lacks an analyte specific ionizing agent 190 on working electrode 112 and on counter electrode 114, as this electrode pair is for analyzing a physical characteristic of the sample. The second electrode pair 120 includes an analyte specific ionizing agent 190 on the working electrode 122 or on the working and counter electrodes 122, 124 that reacts with a single analyte, thus providing specificity to a portion of the generated electrical output. For analysis, the sample is introduced through inlet port 170 and contacts the first and then the second electrode pairs 110, 120.

The working and counter electrodes of the first and/or second electrode pair may be reversed in relation to their proximity to the inlet port 170. The first and second electrode pairs 110, 120 may be reversed in relation to the inlet port 170, if the analyte specific ionizing agent 190 of the second electrode pair 120 does not solubilize sufficiently in the sample when crossed by the sample to reach the first electrode pair 110. Preferably, the first working and counter electrode pair 110 are closer in proximity to the inlet port 170 than the second electrode pair 120 to reduce the possibility of contamination of the first electrode pair 110 by the analyte specific ionizing agent 190 of the second electrode pair 120.

The substrate 180 of the test sensor 100 may be made from any non-electrically conductive substrate material that is compatible with the analysis. Example substrate materials for the substrate 180 include polyethylene terephthalate (PET), polycarbonate (PC), polyimide (PI), polyethylene (PE), polypropylene (PP), polystyrene (PS), polyvinyl chloride (PVC), polyoxymethylene (POM), monomer-cast nylon (MC), polybutylene terephthalate (PBT), methacrylic resin (PMMA), ABS resin (ABS), glass, ceramic, and the like. The test sensor 100 is shown without a lid, which forms a sample reservoir 175 including the electrode pairs and the inlet port 170. After traveling through the inlet port 170, the sample enters the sample reservoir 175 and contacts the electrode pairs. The lid is on the substrate 180 and may be made from a non-electrically conductive substrate material that is compatible with the analysis, similarly to the material of the substrate 180. The lid may be bonded directly to the substrate 180 or may be separated from the substrate 180 by one or more spacers.

The electrical conductors 132, 134, 142, and 144 are on the substrate 180 of the test sensor 100. The electrical conductors 132, 134, 142, and 144 establish electrical communication with the electrical conductor contacts 152, 154, 162, and 164 of the test sensor 100 that in turn establish electrical communication between the contacts of the measurement device (not shown) and the electrode pairs 110, 120. Thus, each electrode 112, 114, 122, and 124 has a corresponding electrical conductor 132, 134, 142, and 144 and a corresponding electrical conductor contact 152, 154, 162, and 164. In this way, the measurement device (not shown) can apply an electrical input and measure a generated electrical output between either electrode pair 110 or 120 or both electrode pairs 110 and 130, as each electrode may be independently addressed. For illustration, two electrode pairs are shown in FIG. 1; however, additional electrodes, such as a reference electrode, or electrode pairs may be included on the test sensor 100. Additional electrical conductors also may extend into the sample reservoir to provide functionality not provided by the electrodes.

The first electrode pair 110 is formed on the electrical conductors 132, 134 by depositing an electrode core on each conductor. Preferably, the electrode core material forming an electrode core is substantially homogeneous, thus not including distinct or substantially distinct layers of different electrode core materials. Both the working electrode 112 and the counter electrode 114 of the first electrode pair 110 may be active electrodes. When both the working and counter electrodes 112, 114 are active electrodes, the electrode core material for both electrodes may include silver and silver chloride salt (Ag/AgCl), the electrode core material for both electrodes may include a mixture of carbon and silver metal (Ag/C), or the electrode core material for one electrode may be Ag/AgCl with the electrode core material for the other electrode being Ag/C. Preferably, the electrode core material for both electrodes includes Ag/AgCl or Ag/C. The first electrode pair 110 also may be formed with an inactive working electrode 112 and an active counter electrode 114, where the electrode core material of the active counter electrode 114 includes silver chloride salt (Ag/AgCl). The first electrode pair 110 lacks an electron transfer mediator, instead relying on at least one active electrode.

When an active electrode is formed using silver-silver chloride (Ag/AgCl), the silver content is from 70% to 90% (weight/weight) of the electrode core material deposited on the electrical conductor after drying. Preferably, the silver content is from 75% to 85% (weight/weight) of the electrode core material deposited on the electrical conductor after drying. The reminder of the electrode core material may be polymeric binders, surfactants, and fillers that do not chemically react or electrochemically participate in the analysis.

The operating potential for the active Ag/AgCl electrodes during the Hct analysis may be from 400 mV to 7,000 mV. Preferably, the operating potential for the active Ag/AgCl electrodes during the Hct analysis is from 400 mV to 4,000 mV. More preferably, the operating potential for the active Ag/AgCl electrodes during the Hct analysis is from 400 mV to 3,500 mV.

When an active electrode is formed using a mixture of carbon and silver metal (Ag/C), the silver metal is from 20% to 60% (weight/weight) of the electrode core material deposited on the electrical conductor after drying. Preferably, the silver metal is from 40% to 60% (weight/weight) of the electrode core material deposited on the electrical conductor after drying. More preferably, the silver metal is from 50% to 60% (weight/weight) of the electrode core material deposited on the electrical conductor after drying. Carbon comprises at least 90% of the non-silver electrode core material for the active Ag/C electrodes.

The operating potential for the active Ag/C electrodes during the Hct analysis may be from 1,000 mV to 7,000 mV. Preferably, the operating potential for the active Ag/C electrodes during the Hct analysis is from 1,500 mV to 4,000 mV. More preferably, the operating potential for the active Ag/C electrodes during the Hct analysis is from 2300 mV to 3,500 mV. Thus, higher operating potentials are preferred for the Ag/C electrodes than for the Ag/AgCl electrodes.

When an inactive carbon working electrode is paired with an active counter electrode, the active counter electrode is formed using silver-silver chloride (Ag/AgCl), the silver content is from 70% to 90% (weight/weight) of the counter electrode core material deposited on the electrical conductor after drying. Preferably, the silver content is from 75% to 85% (weight/weight) of the counter electrode core material deposited on the electrical conductor after drying. The reminder of the electrode core material may be polymeric binders, surfactants, and fillers that do not chemically react or electrochemically participate in the analysis. The inactive carbon working electrode core material is substantially carbon and does not undergo an electrochemical redox reaction during the analysis. Other core materials, such as platinum or gold metal, may be used in place of carbon for the inactive carbon working electrode.

The operating potential for the inactive carbon working electrode paired with the active Ag/AgCl counter electrode during the Hct analysis may be from 2,000 mV to 10,000 mV. Preferably, the operating potential for the active Ag/C electrodes during the Hct analysis is from 2,300 mV to 7,000 mV. More preferably, the operating potential for the active Ag/C electrodes during the Hct analysis is from 2,500 mV to 6,000 mV. Thus, higher operating potentials are preferred for the inactive carbon working and active Ag/AgCl counter electrodes than for the Ag/AgCl or Ag/C electrode pairs.

The second electrode pair 120 is formed on the electrical conductors 142, 144 by depositing at least one electrode core material on each conductor to form the electrodes. An electron transfer mediator is then deposited on at least one of the electrodes, and the analyte specific ionizing agent 190 is deposited on at least the working electrode 122. Preferably, the electrodes of the second electrode pair 120 are inactive to prevent interference with the electron transfer mediator and especially the analyte specific ionizing agent during storage and use of the test sensor 100. As an active electrode can undergo a redox reaction during the analysis, this reaction can generate an electrical output in addition to the desired electrical output responsive to the charged electron transfer mediator. Also, the electrode core material of an active electrode can degrade the analyte specific ionizing agent and/or the electron transfer mediator during storage of the test sensor 100 leading to poor accuracy of the analyte concentration determined for the sample. When the analyte specific ionizing agent is an enzyme, the use of an active electrode for the second electrode pair 120 can cause significant inactivation of the enzyme or denaturing during storage.

An electron transfer mediator is not needed or desired on the first electrode pair 110 during the analysis. In this respect, "on" also includes the situation where the electron transfer mediator is arranged in the test sensor so that the electron transfer mediator solubilizes and is carried on the first electrode pair 110 during the analysis of the sample. An electron transfer mediator is not deposited on the counter electrode 114 of the first electrode pair 110 of the test sensor 100. Preferably, an electron transfer mediator is not deposited on the counter electrode 114 or the working electrode 114 of the first electrode pair 110 of the test sensor 100.

FIG. 2 represents a test sensor 200 having at least four electrodes, with a first working and counter electrode pair 210 for analyzing a physical characteristic, such the Hct content, of the sample and a second working and counter electrode pair 220 for analyzing an analyte in the sample. As previously discussed in regard to FIG. 1, the sample crosses the first electrode pair 210 before reaching the second electrode pair 220. Thus, as in test sensor 100 of FIG. 1, the second electrode pair 220 is used to determine the analyte concentration of the sample with an analyte specific ionizing agent 290. The test sensor 200 is similar to the test sensor 100 of FIG. 1, other than the working electrodes 212, 222 of the first and second electrode pairs 210, 220, respectively, share a single electrical conductor 233 and electrical conductor contact 253. Similarly, the counter electrodes 214, 224 of the first and second electrode pairs 210, 220, respectively, share a single electrical conductor 235 and electrical conductor contact 255. This does not significantly change the electrochemical analysis performed by the test sensor 200 in relation to that of the test sensor 100 of FIG. 1, other than both the first and second electrode pairs 210 and 220 of the test sensor 200 apply a potential through the sample at substantially the same time. Thus, in the sensor 200, the measurement device (not shown) cannot apply a potential to the first or the second electrode pair without applying the potential to the remaining electrode pair.

FIG. 3 represents a test sensor 300 having at least four electrodes, with a first working and counter electrode pair 310 for analyzing the Hct content of the sample and a second working and counter electrode pair 320 for analyzing an analyte in the sample. However, the test sensor 300 separates the first working and the counter electrode pair 310 from the second working and counter electrode pair 320 by placing each of the different electrode pairs in a branch of the sample reservoir. Unlike the test sensor 100 of FIG. 1, which has a linear sample reservoir, the test sensor 300 includes an inlet port 370 where after entering the sample separates into a first reservoir branch 372 and a second reservoir branch 374. The first electrode pair 310 may reside in the first reservoir branch 372, while the second electrode pair 320 may reside in the second reservoir branch 374. This "branched reservoir design" reduces the chance that analyte specific ionizing agent 390 or the electron transfer mediator (not shown) deposited on the second electrode pair 320 could reach the first electrode pair 310 during the analysis. In relation to the test sensor 100 of FIG. 1, the test sensor 300 of FIG. 3 may be used for analyses of longer duration or with reagents having a greater solubility in the sample and may require a smaller sample volume to cover the electrodes. The electrical conductors and electrical conductor contacts of the test sensor 300 are similar in design and have the same operability as those of the test sensor 100 of FIG. 1.

FIG. 4 represents a test sensor 400 having at least four electrodes, with a first working and counter electrode pair 410 for analyzing the Hct content of the sample and a second working and counter electrode pair 420 for analyzing an analyte in the sample. The test sensor 400 takes the chemical separation of the first and second electrode pairs 410, 420 a step further by placing each electrode pair in a different reservoir branch separated by the inlet port 470. Thus, after entering the test sensor 400 through the central inlet port 470, the sample flows to the first reservoir branch 472 that may include the first electrode pair 410 and flows in the opposite direction to the second reservoir branch 474 that may include the second electrode pair 420. This "branched reservoir design" reduces the chance that analyte specific ionizing agent 490 or the electron transfer mediator (not shown) deposited on the second electrode pair 420 could reach the first electrode pair 410 during the analysis. In relation to the test sensor 100 of FIG. 1, the test sensor 400 of FIG. 4 may be used for analyses of longer duration or with reagents having a greater solubility in the sample and may require a smaller sample volume to cover the electrodes. The electrical conductors and electrical conductor contacts of the test sensor 400 are similar in design and have the same operability as those of the test sensor 100 of FIG. 1.

FIG. 5 represents a test sensor 500 having at least two electrodes, with a first working and counter electrode pair 510 for analyzing a physical characteristic, such as the Hct content, of the sample. In addition to the Hct content of the sample, the test sensor 500 may be used to determine blood viscosity. The first electrode pair 510 lacks the analyte specific ionizing agent on working electrode 512 and on counter electrode 514. The test sensor 500 also lacks a second working and counter electrode pair for providing specificity to a portion of the generated output and thus for analyzing an analyte in the sample. For analysis, the sample is introduced through inlet port 570 and contacts the first electrode pair 510.

The substrate 580 of the test sensor 500 may be made from any non-electrically conductive substrate material that is compatible with the analysis, as previously discussed in the context of FIG. 1.

The electrical conductors 532 and 534 are on the substrate 580 of the test sensor 500. The electrical conductors 532 and 534 establish electrical communication with the electrical conductor contacts 552 and 554 that in turn establish electrical communication between the contacts of the measurement device (not shown) and the first electrode pair 510 of the test sensor 500. Thus, each electrode 512, 514 has a corresponding electrical conductor 532, 534 and a corresponding electrical conductor contact 552, 554. In this way, the measurement device can apply an electrical input and measure a generated electrical output between the electrode pair 510. For illustration, one electrode pair is shown in FIG. 5; however, additional non-analyte specific electrodes, such as a reference electrode, or electrode pairs may be included on the substrate 580. Additional electrical conductors also may extend into the sample reservoir to provide functionality not provided by the electrodes.

The first electrode pair 510 of the test sensor 500 may be formed on the electrical conductors 532 and 534 as previously described for the electrode pair 110 of test sensor 100 in the context of FIG. 1. Both the working electrode 512 and the counter electrode 514 of the first electrode pair 510 may be active electrodes. When both the working and counter electrodes 512, 514 are active electrodes, the electrode core material for both electrodes may include silver-silver chloride (Ag/AgCl), the electrode core material for both electrodes may include a mixture of silver metal and carbon (Ag/C), or the electrode core material for one electrode may be Ag/AgCl with the electrode core material for the other electrode being Ag/C. Preferably, the electrode core material for both electrodes includes silver-silver chloride (Ag/AgCl). The first electrode pair 510 also may be formed with an inactive working electrode 512 and an active counter electrode 514, where the electrode core material of the active counter electrode 514 includes silver-silver chloride (Ag/AgCl). The first electrode pair 510 lacks an electron transfer mediator, instead relying on at least one active electrode.

The active electrode/s of the first electrode pair 510 of the test sensor 500 may be formed and operated at potentials in accord with the first electrode pair 110 of the test sensor 100 in the context of FIG. 1. An electron transfer mediator is not needed or desired on the first electrode pair 510 during the analysis as previously described in the context of FIG. 1 for the first electrode pair 110.

Figure 6:
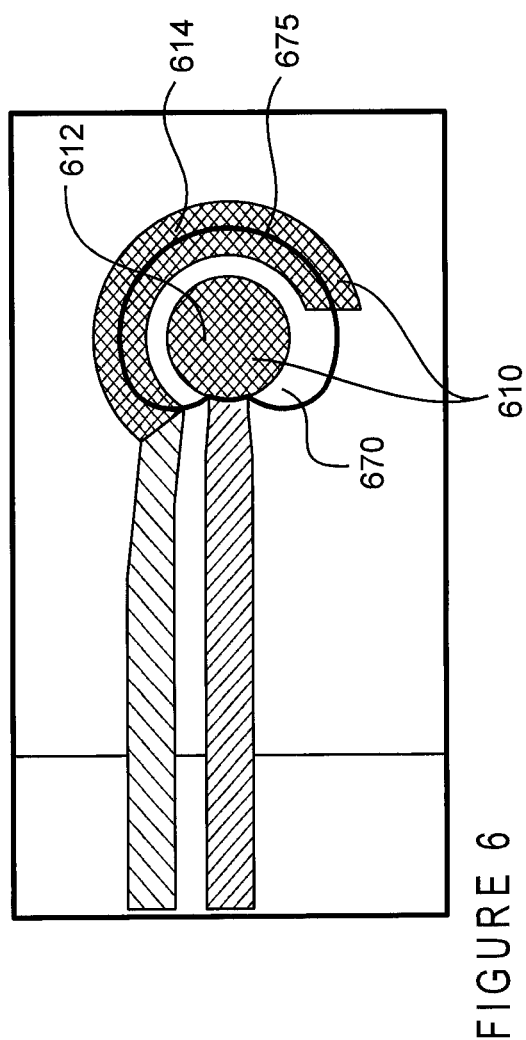
FIG. 6 represents a test sensor having at least two electrodes, with a first working and counter electrode pair for analyzing a physical characteristic, such as the Hct content, of the sample.

FIG. 6 represents a test sensor 600 having at least two electrodes, with a first working and counter electrode pair 610 for analyzing a physical characteristic, such as the Hct content, of the sample. In addition to the Hct content of the sample, the test sensor 600 may be used to determine blood viscosity. The first electrode pair 610 lacks the analyte specific ionizing agent on working electrode 612 and on counter electrode 614. The test sensor 600 also lacks a second working and counter electrode pair for providing specificity to a portion of the generated output and thus for analyzing an analyte in the sample. For analysis, the sample is introduced through inlet port 670 and contacts the first electrode pair 610. The test sensor 600 provides a circular sample reservoir 675 in relation to the linear sample reservoir of the test sensor 500 of FIG. 5. The test sensor 600 is similar to the test sensor 500 of FIG. 5 other than sample inlet 670 is centrally located over working electrode 612, which has a much greater surface area than the working electrode of the test sensor 500 of FIG. 5. After entry, the sample flows over the working electrode 612 and outward over counter electrode 614, which also has a much greater surface area than the counter electrode of the test sensor 500 of FIG. 5. The concentric circular arrangement of the working and counter electrodes 612, 614 of the test sensor 600 provide the advantage of a more uniform electrical field around the working electrode 612. The enhanced uniformity of the electrical field around the working electrode 612 provides a more precise electrochemical response and better reagent coverage when reagents are deposited as a single drop from a pipette tip in relation to the test sensor 500 of FIG. 5. The electrical conductors and electrical conductor contacts of the test sensor 600 are similar in design and have the same operability as those of the test sensor 500 of FIG. 5.

Figure 7:
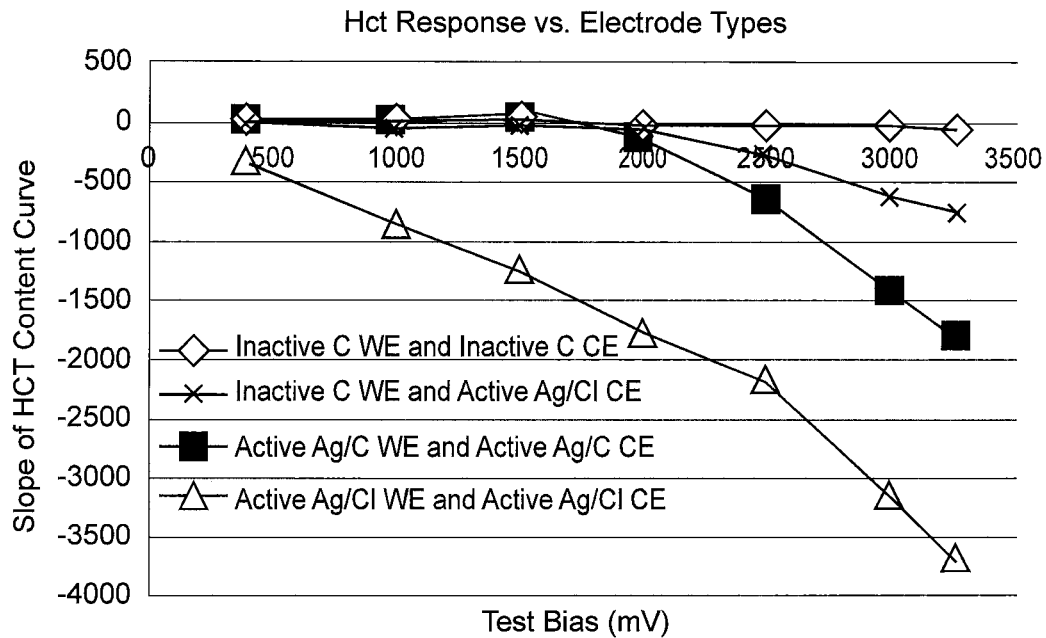
FIG. 7 relates test bias in mV vs. slope of multiple Hct contents (~28%-55% v/v) and confirms that an Hct responsive electrical output is obtained from a test sensor when inactive electrodes are replaced with the active electrodes.

FIG. 7 relates test bias in mV vs. slope of multiple Hct contents (~28%-55% v/v) and confirms that an Hct responsive electrical output is obtained from a test sensor when inactive electrodes are replaced with the active electrodes, as previously described. As the Y-axis of the graph provides the electrical output (in nanoamps (nA)) divided by the known Hct content of the blood sample, the greater the departure from 0 over the 500 to 3500 millivolt (mV) electrical input range (the X-axis), the greater the Hct response for the tested electrodes. A useful Hct response is observed when the absolute value of the HCT response curve is greater than 250.

In FIG. 7, inactive electrodes provided a substantially flat Hct "response" when a DC electrical input was applied to blood samples containing varying Hct contents. An inactive carbon working electrode paired with an active Ag/AgCl electrode provide a useful Hct response above approximately 1,500 mV. While the graph ends at 3,500 mV, we believe DC inputs above 3,500 mV would continue to show a useful Hct response. Active Ag/C working and counter electrodes provided a useful Hct response above approximately 1,000 mV. While the graph ends at 3,500 mV, we believe DC inputs above 3,500 mV would continue to show a useful Hct response. Active Ag/AgCl working and counter electrodes provided a useful Hct response above approximately 300 mV and provided the greatest Hct response of these active electrodes.

Figure 8A:
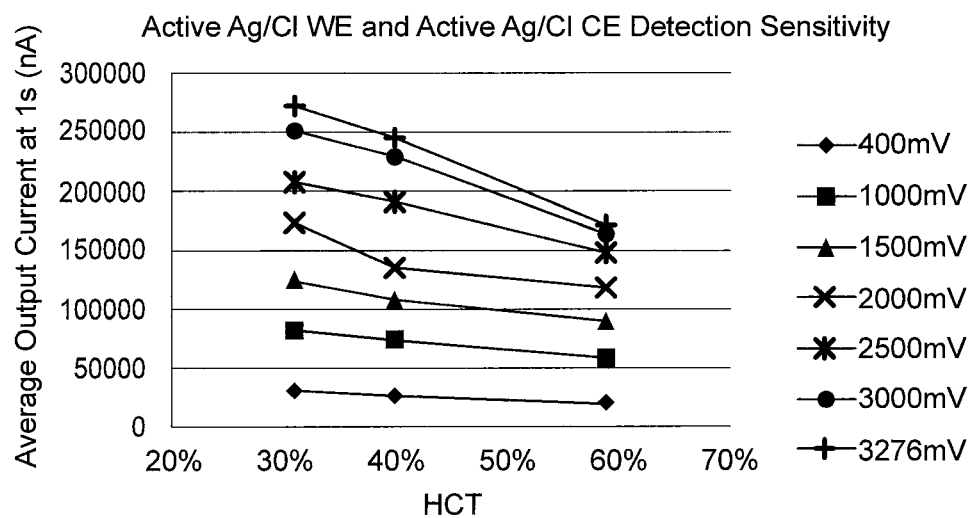
FIG. 8A provides the detection sensitivity for a test sensor having active Ag/AgCl working and counter electrodes.

FIG. 8A provides the detection sensitivity, thus how much change in generated electrical output is observed over a range of different Hct blood sample contents, for a test sensor having active Ag/AgCl working and counter electrodes. The greater the absolute value of the slope of the line when the generated electrical outputs are plotted against the Hct content of the blood sample, the greater the change in the generated electrical outputs and the greater the detection sensitivity. Slopes having an absolute value greater than 30 are considered useful in the context of detection sensitivity when the analysis is performed at 25° C. with the Hct percentages and electrical input potentials shown in the figure. Preferably, slopes having an absolute value greater than 100 are considered useful in the context of detection sensitivity when the analysis is performed at 25° C. with the Hct percentages and electrical input potentials shown in the figure. More preferably, slopes having an absolute value greater than 200 are considered useful in the context of detection sensitivity when the analysis is performed at 25° C. with the Hct percentages and electrical input potentials shown in the figure.

In FIG. 8A, generated electrical outputs in the form of current (nA) are plotted on the Y-axis and the known percent Hct (volume/volume) of the blood sample are plotted on the X-axis. DC electrical inputs from 400 mV to 3276 mV were used and the generated outputs were measured after approximately 1 second of introducing the blood sample to the test sensors. The data was recorded at approximately 25° C., but other temperatures consistent with the analysis may be used.

Table 8, below, provides the generated output currents from the electrical inputs at Hct contents between approximately 30% and 60% (volume/volume) for a test sensor having active Ag/AgCl working and counter electrodes from FIG. 8A. Hct contents of 20% and 70% also are depicted on the FIG. 8A X-axis, as while not tested, we believe useful Hct detection sensitivities also would be observed at these Hct sample contents. The line slopes also are shown, and slopes sufficient to provide useful detection sensitivity were provided by electrical inputs at and above 400 mV. While electrical inputs above 3,276 mV are not shown, we believe DC inputs above 3,276 mV would continue to provide useful detection sensitivity.

TABLE 8

| Sample HCT | 400 mV | 1000 mV | 1500 mV | 2000 mV | 2500 mV | 3000 mV | 3276 mV |
|---|---|---|---|---|---|---|---|
| 31% | 28967 | 82133 | 124667 | 172000 | 207000 | 250000 | 271133 |
| 40% | 24233 | 72667 | 106750 | 1134133 | 190333 | 228500 | 244333 |
| 59% | 18900 | 57800 | 88367 | 117667 | 147000 | 163333 | 169333 |
| Slope (nA/% HCT) | −347 | −856 | −1245 | −1774 | −2164 | −3147 | −3684 |

Figure 8B:
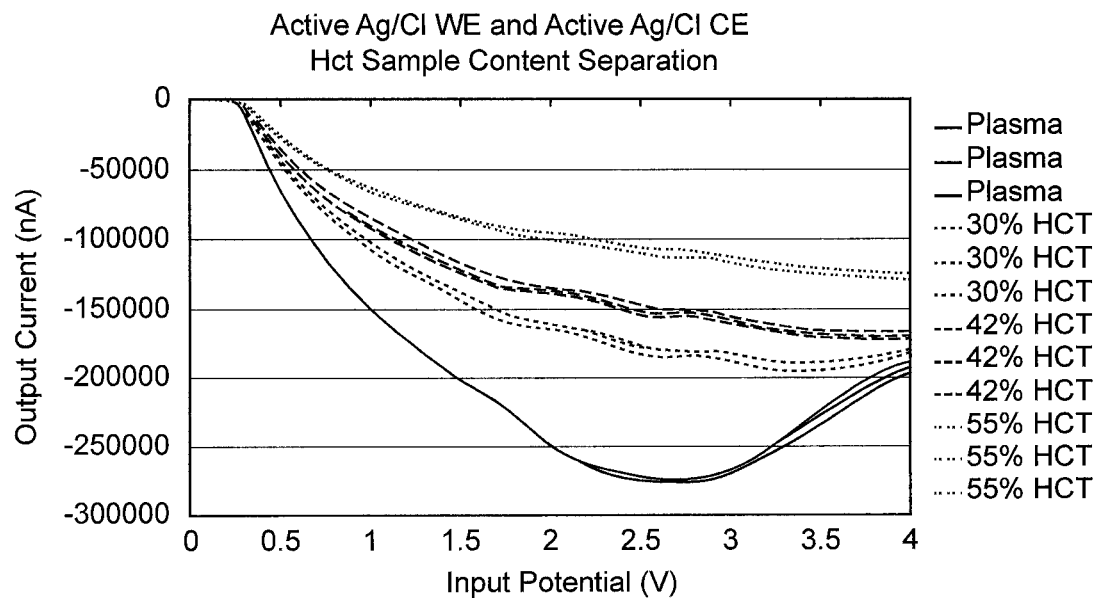
FIG. 8B demonstrates the ability of a test sensor having active Ag/AgCl working and counter electrodes to generate different electrical outputs for different known Hct contents of samples.

FIG. 8B demonstrates the ability of a test sensor having active Ag/AgCl working and counter electrodes to generate different electrical outputs for different known Hct contents of samples using an electrical input where the potential applied across the working and counter electrodes of the test sensor changed with time. This is another measure of detection sensitivity as the greater the difference in electrical output for different Hct sample contents the more easily the biosensor system can differentiate different Hct sample contents and the greater the detection sensitivity of the biosensor system.

In FIG. 8B, generated electrical outputs in the form of current (in amps (A)) are plotted on the Y-axis and the electrical inputs in the form of potential (in Volts (V)) are plotted on the X-axis. The electrical input was swept from 0 V to approximately 4 V at a rate of approximately 500 mV per second. The test sensor differentiated 0% Hct (plasma), 30% Hct, 42% Hct, and 55% Hct content blood samples with different generated output currents with DC input voltages above approximately 0.4 Volts. The ability to differentiate the Hct contents increased up to approximately 3.5 Volts, but remained useful at 4 Volts. While not tested, we believe DC input voltages above 4 Volts would not remain useful in providing different electrical outputs for different Hct contents of samples.

Figure 9A:
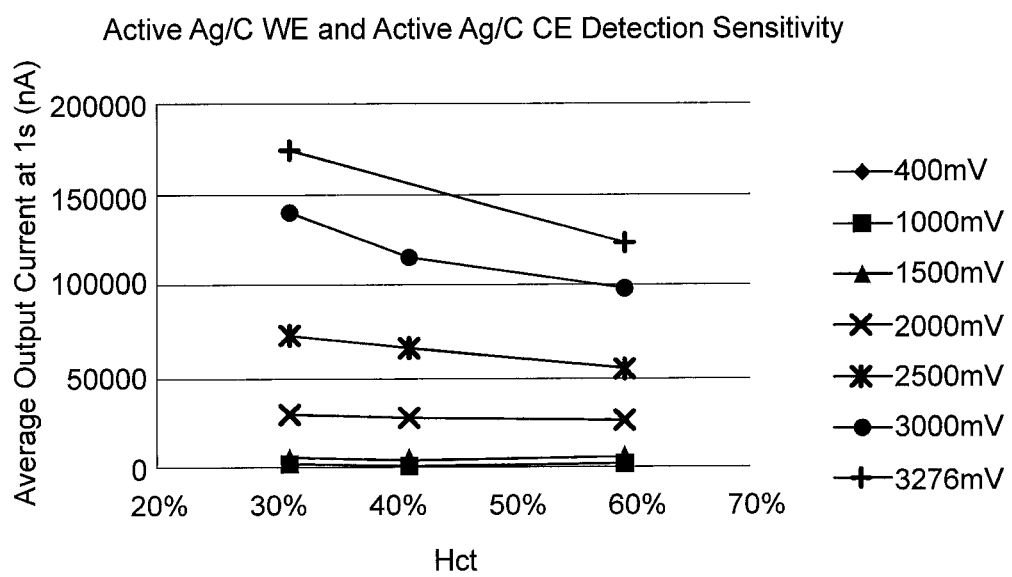
FIG. 9A provides the detection sensitivity for a test sensor having active Ag/C working and counter electrodes.

FIG. 9A provides the detection sensitivity for a test sensor having active Ag/C working and counter electrodes using an electrical input where the potential applied across the working and counter electrodes of the test sensor is substantially constant as a function of time. The electrical inputs and analysis conditions were as previously described in relation to FIG. 8A.

Table 9, below, provides the generated output currents from the electrical inputs at Hct contents between approximately 30% and 60% for the test sensor having active Ag/C working and counter electrodes from FIG. 9A. Hct sample contents of 20% and 70% also are depicted, as while not tested, we believe useful Hct detection sensitivities also would be observed at these Hct sample contents. The line slopes also are shown, and slopes sufficient to provide useful detection sensitivity were provided by electrical inputs at and above 1,000 mV. While electrical inputs above 3,276 mV are not shown, we believe DC electrical inputs above 3,276 mV would continue to provide useful detection sensitivity.

TABLE 9

| Sample HCT | 400 mV | 1000 mV | 1500 mV | 2000 mV | 2500 mV | 3000 mV | 3276 mV |
|---|---|---|---|---|---|---|---|
| 31% | 270 | 3037 | 6567 | 30367 | 72967 | 140333 | 174333 |
| 41% | 158 | 2513 | 6250 | 28300 | 66933 | 116667 | N/A |
| 59% | 231 | 3093 | 7940 | 25700 | 54933 | 99000 | 123333 |
| Slope (nA/% HCT) | −0.758 | 5.62 | 54.4 | −164 | −647 | −1417 | −1821 |

Figure 9B:
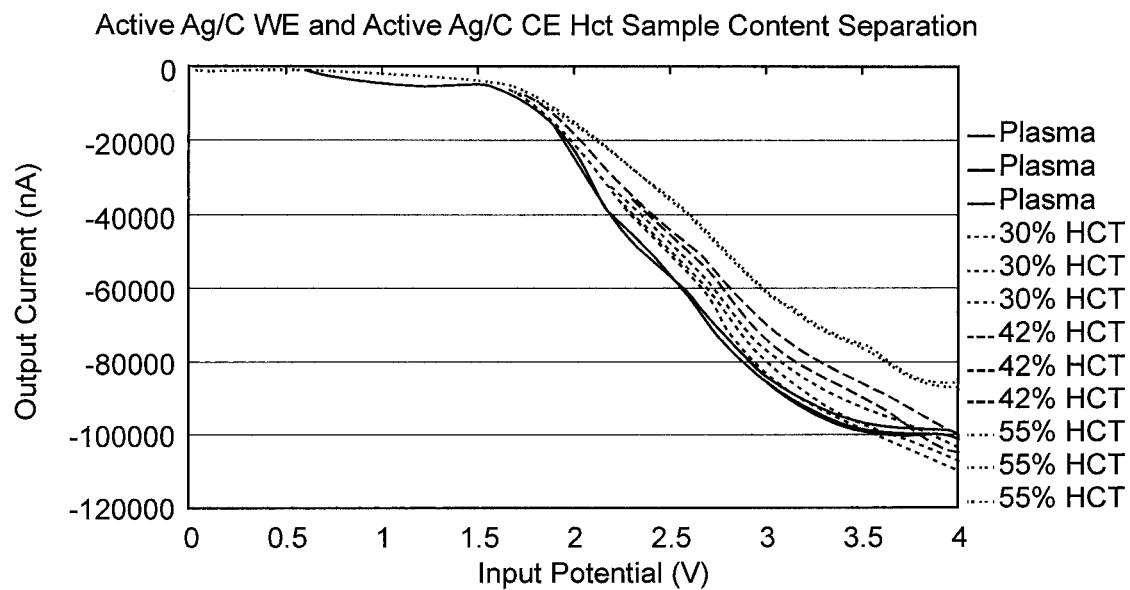
FIG. 9B demonstrates the ability of a test sensor having active Ag/C working and counter electrodes to generate different electrical outputs for different known Hct contents of samples.

FIG. 9B demonstrates the ability of a test sensor having active Ag/C working and counter electrodes to generate different electrical outputs for different known Hct contents of samples using an electrical input where the potential applied across the working and counter electrodes of the test sensor changed with time. The electrical inputs, Hct contents of the tested samples, and analysis conditions were as previously described in relation to FIG. 8B. The test sensor differentiated 0% Hct (plasma), 30% Hct, 42% Hct, and 55% Hct content blood samples with different generated output currents with DC input voltages above approximately 1 Volt. The ability to differentiate the Hct contents increased up to 4 Volts. While not tested, we believe DC input voltages above 4 Volts would not remain useful in providing different electrical outputs for different Hct contents of samples.

Figure 10A:
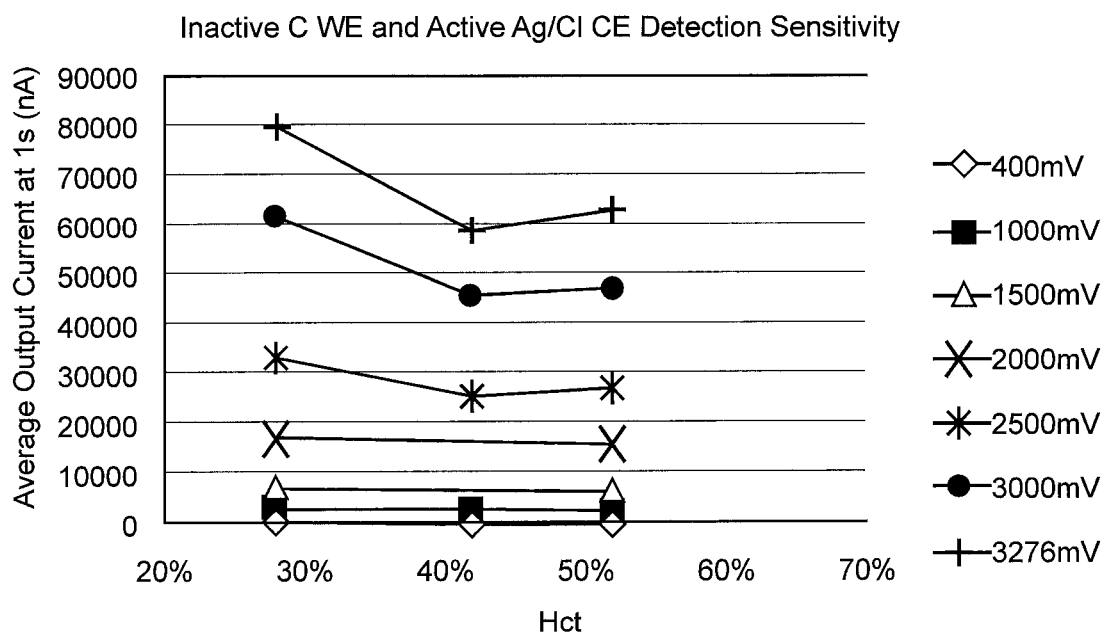
FIG. 10A provides the detection sensitivity for a test sensor having an inactive carbon working electrode and an active Ag/AgCl counter electrode.

FIG. 10A provides the detection sensitivity for a test sensor having an inactive carbon working electrode and an active Ag/AgCl counter electrode using an electrical input where the potential applied across the working and counter electrodes of the test sensor is substantially constant as a function of time. The electrical inputs and analysis conditions were as previously described in relation to FIG. 8A.

Table 10, below, provides the generated output currents from the electrical inputs at Hct contents between 28% and 52% from FIG. 10A. Hct sample contents of 20%, 60%, and 70% also are depicted on the X-axis of FIG. 10A, as while not tested, we believe useful Hct detection sensitivities also would be observed at these Hct sample contents. The line slopes also are shown, and slopes sufficient to provide useful detection sensitivity were provided by electrical inputs above 2000 mV. While electrical inputs above 3,276 mV are not shown, we believe DC inputs above 3,276 mV would continue to provide useful detection sensitivity.

TABLE 10

| Sample HCT | 400 mV | 1000 mV | 1500 mV | 2000 mV | 2500 mV | 3000 mV | 3276 mV |
|---|---|---|---|---|---|---|---|
| 28% | 108 | 3070 | 6943 | 17367 | 331333 | 61300 | 79767 |
| 42% | 78 | 2173 | N/A | N/A | 24933 | 45367 | 58500 |
| 52% | 118 | 2263 | 6250 | 16233 | 27233 | 47233 | 63000 |
| Slope (nA/% HCT) | 0 | −36 | −29 | −47 | −268 | −622 | −751 |

Figure 10B:
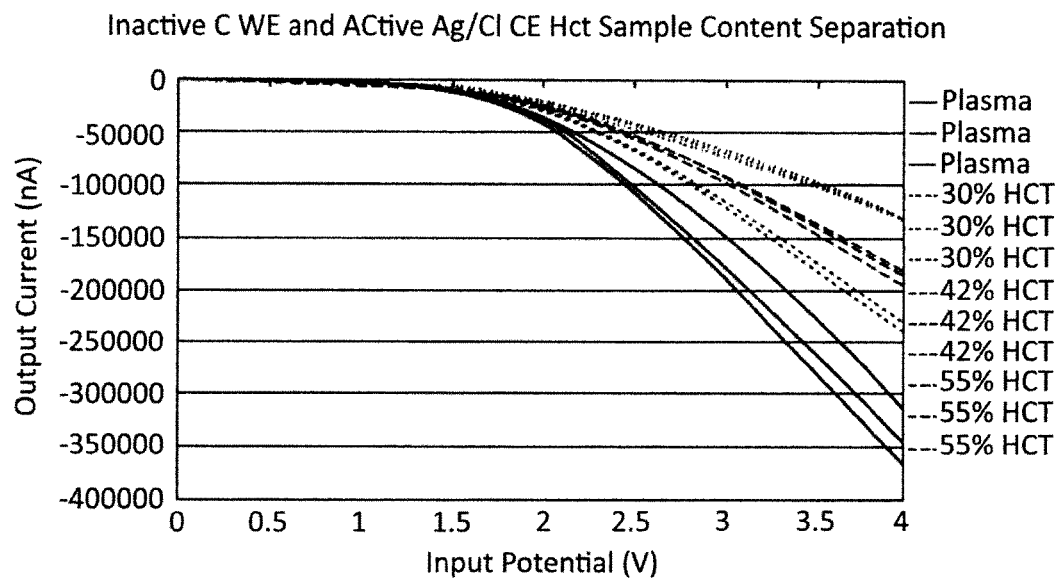
FIG. 10B demonstrates the ability of a test sensor having an inactive carbon working electrode and an active Ag/AgCl counter electrode to provide different electrical outputs for different known Hct contents of samples.

FIG. 10B demonstrates the ability of a test sensor having an inactive carbon working electrode and an active Ag/AgCl counter electrode to provide different electrical outputs for different known Hct contents of samples using an electrical input where the potential applied across the working and counter electrodes of the test sensor changed with time. The electrical inputs, Hct content of the tested samples, and analysis conditions were as previously described in relation to FIG. 8B. The test sensor differentiated 0% Hct (plasma), 30% Hct, 42% Hct, and 55% Hct content blood samples with different generated output currents with DC input voltages above approximately 2 Volts. The ability to differentiate the Hct contents increased up to 4 Volts. While not tested, we believe DC input voltages above 4 Volts would remain useful in providing different electrical outputs for different Hct contents of samples.

Figure 11:
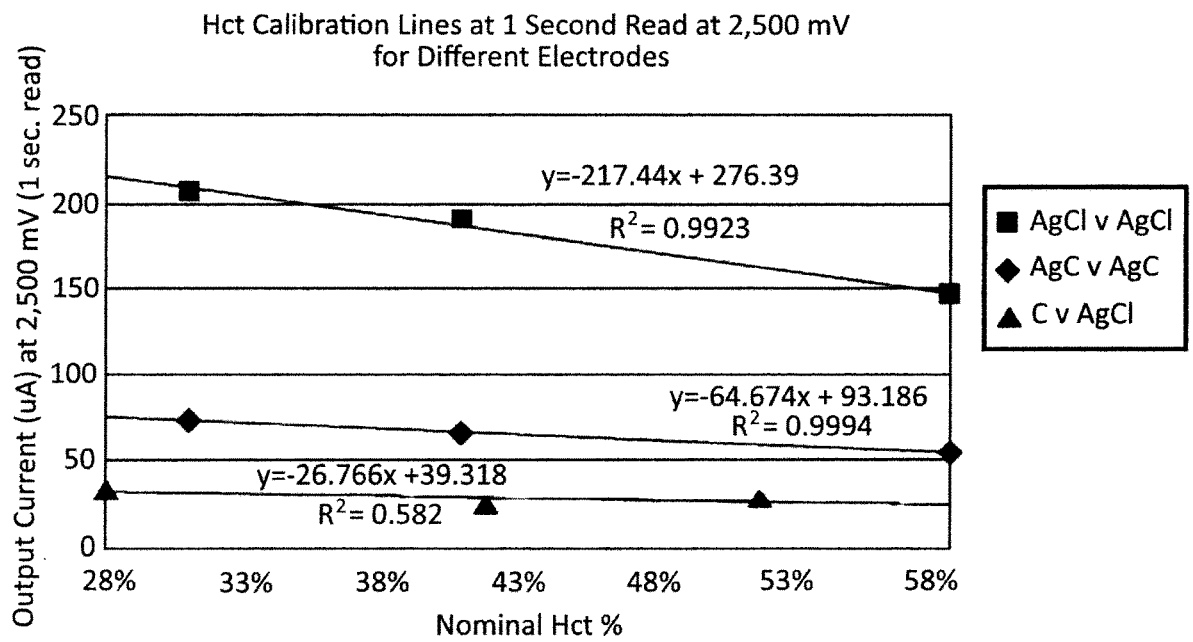
FIG. 11 plots electrical output currents generated from a 2.5 V electrical input for the three previously described electrode combinations at multiple known Hct sample contents.

FIG. 11 plots electrical output currents generated from a 2.5 V electrical input for the three previously described electrode combinations at multiple known Hct sample contents. The substantial linearity of the lines between 28% and 58% Hct sample content establishes that a single electrical input amount will generate electrical outputs that decrease substantially constantly with increasing Hct sample content. The slopes of the lines for the different electrode combinations reflect the detection sensitivity. In relation to the inactive carbon working and active Ag/AgCl counter electrodes (slope of −268), the active Ag/C counter and working electrodes demonstrated about 2.4 times the sensitivity (slope −648), and the active Ag/AgCl working and counter electrodes demonstrated about 8 times the sensitivity (slope −2164). Thus, while the dual active electrode test sensors demonstrate greater detection sensitivity than the inactive/active electrode pair, all pairs provide a useful Hct response for the biosensor system.

Figure 12:
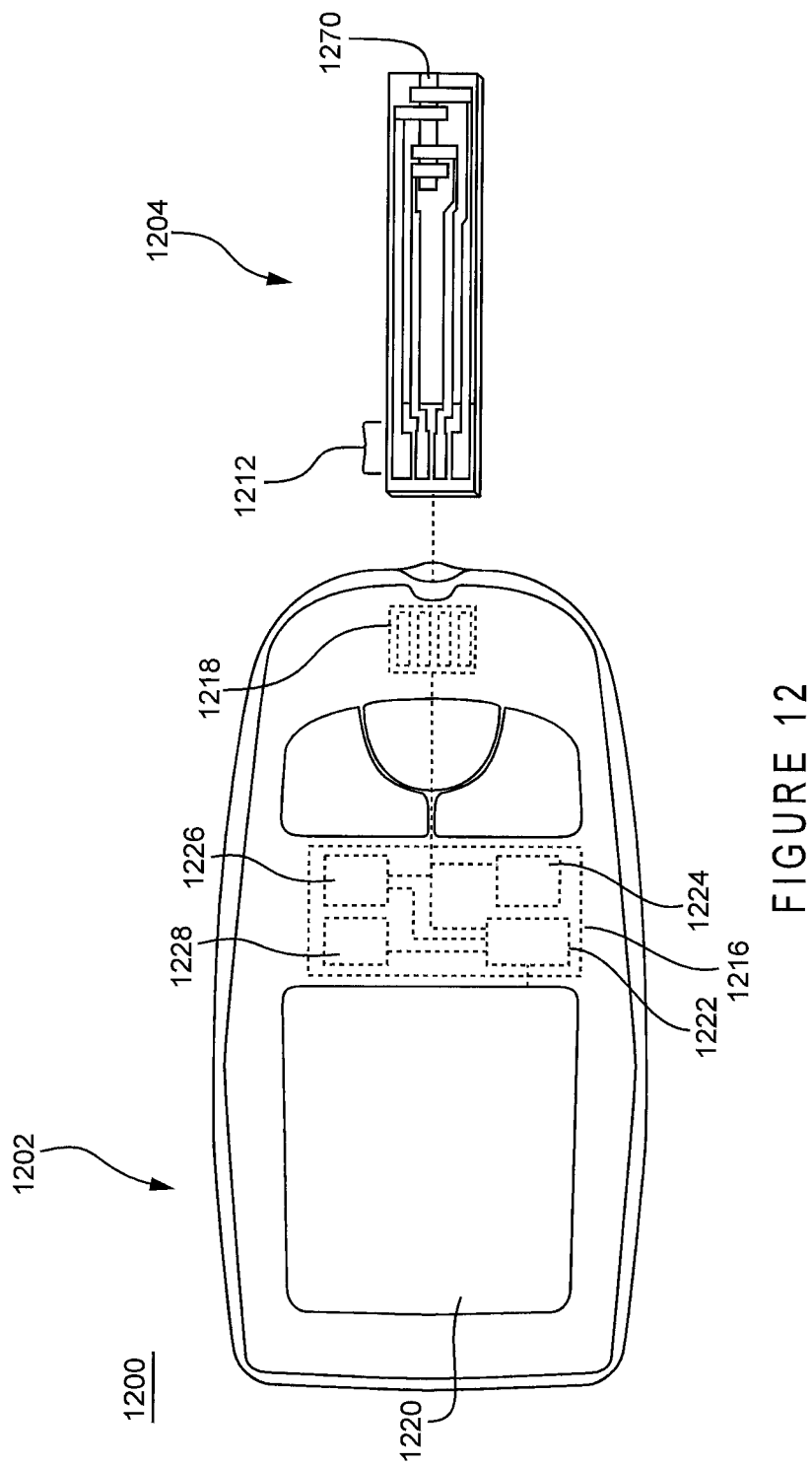
FIG. 12 depicts a schematic representation of an electrochemical biosensor system that determines an analyte concentration in a sample or a physical characteristic of the sample.

FIG. 12 depicts a schematic representation of an electrochemical biosensor system 1200 that determines an analyte concentration in a sample or a physical characteristic of the sample. Biosensor system 1200 includes a measurement device 1202 and a test sensor 1204, which may be implemented in any analytical instrument, including a bench-top device, a portable or hand-held device, or the like. The biosensor system 1200 may determine the analyte concentration of the sample by correcting the generated output from a second electrode pair including an analyte specific ionizing agent with the generated output from a first electrode pair. The biosensor system 1200 may determine a physical characteristic of a sample from a first electrode pair lacking an analyte specific ionizing agent. While a particular configuration is shown, the biosensor system 1200 may have other configurations, including those with additional components.

The measurement device 1202 includes circuitry 1216 that connects to contacts 1218 of the measurement device 1202. The circuitry 1216 includes a processor 1222 connected to an electrical input generator 1224, an optional temperature sensor 1226, and a storage medium 1228.

The electrical input generator 1224 provides an electrical input to the contacts 1218 in response to the processor 1222. The electrical input is transmitted from the contacts 1218 of the measurement device 1202 to the electrical conductor contacts 1212 and electrodes of the test sensor 1204. The electrical input may be a potential or current and may be constant, variable, or a combination thereof, such as when an AC input is applied with a DC offset. The electrical input may be applied as a single pulse or in multiple pulses, sequences, or cycles. The electrical input generator 1224 also may record a generated electrical output from the electrical conductor contacts 1212 as a generator-recorder.

The optional temperature sensor 1226 determines the temperature of the sample in the reservoir of the test sensor 1204. The temperature of the sample may be measured, calculated from an electrical output, or assumed to be the same or similar to a measurement of the ambient temperature or the temperature of the measurement device 1202. The temperature may be measured using a thermister, thermometer, or other temperature sensing device. Other techniques may be used to determine the sample temperature.

The storage medium 1228 may be a magnetic, optical, or semiconductor memory, another storage device, or the like. The storage medium 1228 may be a fixed memory device, a removable memory device, such as a memory card, remotely accessed, or the like.

The processor 1222 implements the analyte analysis and correction or physical characteristic analysis using computer readable software code and data stored in the storage medium 1228. The processor 1222 may start the analysis in response to the presence of the electrical conductor contacts 1212 of the test sensor 1204, the application of a sample to the test sensor 1204, in response to user input, or the like. The processor 1222 directs the electrical input generator 1224 to provide the electrical input to the contacts 1218. The processor 1222 receives the generated electrical output from the electrical conductor contacts 1212 of the test sensor 1204 through the contacts 1218 of the measurement device 1202. The electrical output from the electrical conductor contacts 1212 is generated in response to the reaction of the analyte in the sample or a physical characteristic of the sample at the electrodes of the test sensor 1204.

The processor 1222 corrects the analyte analysis for a physical characteristic, such as the Hct content, of the sample or determines the physical characteristic of the sample. The determination of the uncorrected analyte concentration of the sample, the physical characteristic content of the sample, or a physical characteristic corrected analyte concentration of the sample from the generated electrical output/s from the test sensor 1204 may be performed with a previously prepared calibration curve and/or a calibration table showing the relationship between the physical characteristic content of the sample, the analyte concentration of the sample, the physical characteristic output measured from the first electrode pair lacking an analyte specific ionizing agent of the test sensor 1204, and the analyte responsive output measured from the second electrode pair of the test sensor 1204 under a specific set of reaction conditions. The results of the analyte or physical characteristic analysis may be output to the display 1220 and may be stored in the storage medium 1228.

The non-transient calibration curve between known analyte concentrations and generated electrical outputs from the test sensor 1204 may be represented graphically, mathematically, a combination thereof, or the like. Non-transient calibration curves may be represented by a fitting equation whose constants, typically represented by a slope and intercept, can be recovered through a non-transient look-up table, or the like that is stored in the storage medium 1228 or by the direct insertion of constants. The fitting equation and any constants of look-up table values in the storage medium 1228 are non-transient. Instructions regarding implementation of the analyte or physical characteristic analysis may be provided by the computer readable software code stored in the storage medium 1228. The code may be object code or any other code describing or controlling the functionality described herein. The data from the analyte or physical characteristic analysis may be subjected to one or more data analysis steps, including the determination of decay rates, ratios, functions, and the like in the processor 1222.

The display 1220 may be analog or digital. The display 1220 may include a LCD, a LED, an OLED, a vacuum fluorescent, or other display adapted to show a numerical reading. Other display types may be used. The display 1220 electrically communicates with the processor 1222. The display 1220 may be separate from the measurement device 1202, such as when in wireless communication with the processor 1222. Alternatively, the display 1220 may be removed from the measurement device 1202, such as when the measurement device 1202 electrically communicates with a remote computing device, medication dosing pump, and the like.

In use, a liquid sample for analysis is transferred into the sample reservoir of the test sensor 1204 by introducing the liquid to the inlet port 1270. The liquid sample flows through the inlet port 1270, filling the reservoir while expelling the previously contained air. If present, the liquid sample chemically reacts with the analyte specific ionizing agent of the second electrode pair after introduction through the inlet port 1270. When the electrical input is applied to the second electrode pair of the test sensor 1204, the electrochemical redox reaction between the ionized analyte or electron transfer mediator begins and an electrical output responsive to the concentration of the analyte in the sample is generated and determined by the processor 1222. When the electrical input is applied to the first electrode pair no chemical reaction occurs, as the first electrode pair lacks an analyte specific ionizing agent. When the electrical input is applied to the first electrode pair, the electrochemical redox reaction with the sample occurs and an electrical output responsive to the physical characteristics of the sample, such as the Hct content of the sample, is generated and determined by the processor 1222. The generated output from the first electrode pair is converted into the physical characteristic content of the sample by the processor 1222. If an analyte responsive electrical output is generated from a second electrode pair, the processor 1222 also may determine an analyte concentration of the sample.

Sample Analyte Concentration Determination in Blood

A test sensor in accord with FIG. 1 having an AgC working and counter electrode first electrode pair was used in combination with a measurement device and an amperometric method to determine the analyte content of a blood sample with Hct sample content correction. While a test sensor in accord with FIG. 1 was used, a test sensor in accord with FIG. 2, FIG. 3, or FIG. 4 may be used, as each test sensor has at least first and second electrode pairs. While the first electrode pair included AgC working and counter electrodes, Ag/AgCl working and counter electrodes, or carbon working and Ag/AgCl counter electrodes also may be used with the appropriate change in input potential, as previously described.

For an example where the analyte of interest is glucose, a blood sample was introduced to the test sensor at approximately 25° C. After approximately 1-2 second from introduction of the sample to the test sensor inlet port, a DC input potential of approximately 400 mV was applied to the second electrode pair including an analyte specific ionizing agent and an electron transfer mediator. In this analysis, the analyte specific ionizing agent was glucose oxidase and the electron transfer mediator was potassium ferricyanide, but different analyte specific ionizing agents and/or electron transfer mediators may be used that are compatible with the analysis, analyte, and sample. A different electrical input potential at the second electrode pair may be beneficial if a different analyte specific ionizing agent and/or electron transfer mediator is used. The electrical output current was measured from the second electrode pair by the measurement device approximately 5 seconds after application of the electrical input. A different introduction and/or electrical input delay may be used, depending on the analysis being performed. The measured output current from the second electrode pair was converted into an uncorrected glucose sample concentration with a previously determined calibration curve relating output currents to sample analyte concentrations.

After applying the input potential to the second electrode pair, an input potential of approximately 2500 mV was applied to the first electrode pair. Approximately 1 second later, the electrical output current was measured from the first electrode pair. A different electrical input potential and/or delay may be used, depending on the analysis being performed. The measured output current from the first electrode pair was converted into a Hct sample concentration with a previously determined Hct calibration curve relating output currents to sample Hct contents.

The electrical output current measured from the first electrode pair was used to determine a correction factor for the uncorrected glucose concentration through multiple mathematical techniques, including continuous and discontinuous functions and offsets. This provided the Hct corrected glucose concentration of the blood sample. While separate glucose and Hct calibration curves and calibration tables were used, these separate correlations could be combined into a single correlation, table, or formula that converts the generated output from the second electrode pair and the generated output from the first electrode pair into a Hct corrected glucose concentration of the sample. Thus, the uncorrected glucose concentration of the sample and the Hct sample content may be determined separately and then converted into a Hct corrected glucose concentration of the sample, or the generated outputs from the first and second electrode pairs may be converted into the Hct corrected glucose concentration of the sample.

Provided below in Tables 11A through 11D for blood samples including 30%, 36%, 42%, 47%, and 55% Hct (v/v) and known glucose concentrations are uncorrected analysis-determined sample glucose concentrations (determined from second electrode pair output currents) and Hct corrected analysis-determined sample glucose concentrations (determined from second and first electrode pair output currents). The hematocrit bias between the uncorrected analysis-determined sample glucose concentrations and the Hct corrected analysis-determined sample glucose concentrations also are provided. These analyses were performed with a test sensor having an active AgC working and AgC counter first electrode pair. While these analyses were performed with AgC working and counter second electrode pairs, Ag/AgCl working and counter second electrode pairs, and inert working and Ag/AgCl counter first electrode pairs also may be used.

TABLE 11A

30% Hct

| Known [Gluc] | Uncorrected [Gluc] | Bias | Hct Corrected [Gluc] | Bias |
|---|---|---|---|---|
| 46.9 | 49 | 2% | 45 | −2% |
| 97.7 | 107 | 9% | 99 | 1% |
| 137 | 160 | 17.1% | 147 | 7.7% |
| 248 | 311 | 25.6% | 276 | 11.4% |
| 378 | 462 | 22.3% | 403 | 6.6% |
| 517 | 604 | 17.0% | 556 | 7.7% |

TABLE 11B

36% Hct

| Known [Gluc] | Uncorrected [Gluc] | Bias | Hct Corrected [Gluc] | Bias |
|---|---|---|---|---|
| 56.7 | 56 | 0% | 53 | −3% |
| 91.5 | 92 | 1% | 88 | −3% |
| 127 | 134 | 5.9% | 127 | −0.1% |
| 268 | 279 | 4.1% | 276 | 2.8% |
| 351 | 385 | 9.7% | 345 | −1.6% |
| 494 | 521 | 5.7% | 500 | 1.2% |

TABLE 11C

42% Hct

| Known [Gluc] | Uncorrected [Gluc] | Bias | Hct Corrected [Gluc] | Bias |
|---|---|---|---|---|
| 53.4 | 54 | 1% | 52 | −2% |
| 102 | 92 | −9.5% | 92 | −9.5% |
| 147 | 140 | −4.4% | 139 | −5.0% |
| 278 | 279 | 0.5% | 276 | −0.6% |
| 399 | 389 | −2.4% | 382 | −4.2% |
| 514 | 510 | −0.9% | 500 | −2.8% |

TABLE 11D

47% Hct

| Known [Gluc] | Uncorrected [Gluc] | Bias | Hct Corrected [Gluc] | Bias |
|---|---|---|---|---|
| 66.5 | 71 | 4% | 71 | 4% |
| 89 | 91 | 2% | 91 | 2% |
| 130 | 132 | 1.5% | 131 | 0.9% |
| 295 | 286 | −3.0% | 290 | −1.7% |
| 414 | 404 | −2.5% | 399 | −3.7% |
| 560 | 542 | −3.2% | 544 | −2.8% |

These results establish that a significant improvement in analysis-determined sample glucose concentrations was observed when the analyte concentration (or currents) obtained from the second electrode pair was corrected with the Hct response currents obtained from the first electrode pair, especially at higher sample glucose concentrations, where improvements of a 100% reduction in Hct bias and greater was observed. While Hct corrected analyte concentrations at the 47% and 42% Hct contents were similar for the higher sample glucose concentrations, significant improvements in the accuracy of the analysis-determined sample glucose concentrations were observed at the 30% and 36% Hct sample contents.

Sample Physical Characteristic Determination for Hct

A test sensor in accord with FIG. 5 having an AgC working and counter electrode first electrode pair was used with a measurement device and an amperometric method to determine the Hct content of blood samples. While a test sensor in accord with FIG. 5 was used, a test sensor in accord with FIG. 6 may be used, as both have a first electrode pair. While the first electrode pair included AgC working and counter electrodes, Ag/AgCl working and counter electrodes, or an inactive working and Ag/AgCl counter electrodes also may be used, as discussed below, with the appropriate change in input potential, as previously described.

A blood sample was introduced to the active AgC first electrode pair test sensor at approximately 25° C. After approximately 1-2 second from introduction of the sample to the test sensor, a DC input potential of approximately 2500 mV was applied to the first electrode pair. Approximately 1 second later the electrical output current was measured from the first electrode pair. Different sample introduction and measurement delays may be used, depending on the analysis being performed. The measured output current from the first electrode pair was converted into a Hct sample content with a previously determined Hct calibration curve relating output currents to sample Hct contents.

Provided below in Table 12 for blood samples including known 30%, 36.5%, 42%, 47.3% and 54.5% Hct (v/v) are analysis-determined Hct contents for three different lots of Ag/C working and counter first electrode pair test sensors.

TABLE 12

| | Lot#1 | | Lot#2 | | Lot#3 | |
|---|---|---|---|---|---|---|
| Hct | Ave Current | Calculated Hct | Ave Current | Calculated Hct | Ave Current | Calculated Hct |
| 30.0% | 46627 | 33.0% | 48224 | 29.4% | 48839 | 28.0% |
| 36.5% | 44082 | 38.7% | 44983 | 36.7% | 44897 | 36.9% |
| 42.0% | 41202 | 45.1% | 43161 | 40.7% | 43544 | 39.9% |
| 47.3% | 40236 | 47.3% | 41675 | 44.1% | 42293 | 42.7% |
| 54.5% | 35364 | 58.2% | 36923 | 54.7% | 36644 | 55.4% |
| Slope (nA/% Hct) | −444 | | −437 | | −457 | |
| Int (nA) | 60183 | | 61375 | | 62473 | |

As can be seen from the table, the analysis-determined Hct content of the samples was substantially representative of the actual Hct content of the samples. For example, when the relative standard deviation (CV %) for each actual Hct sample content was averaged, the Lot 1 test sensors provided an average relative standard deviation of only 5.9% across all the calculated Hct values in relation to the actual values. When these lot averages were averaged across the three different test sensor lots, the active electrode equipped test sensors also showed excellent precision with a value of about 5.3%. The line slopes obtained also establish the excellent detection sensitivity provided by the active electrode pair equipped test sensors.

A test sensor in accord with FIG. 5 having an Ag/AgCl working and counter electrode first electrode pair was used with a measurement device and an amperometric method to determine the Hct content of blood samples. While a test sensor in accord with FIG. 5 was used, a test sensor in accord with FIG. 6 may be used, as both have a first electrode pair.

A blood sample was introduced to the active Ag/AgCl first electrode pair test sensor at approximately 25° C. After approximately 1-2 second from introduction of the sample to the test sensor, a DC input potential of approximately 400 mV was applied to the first electrode pair. Approximately 1 second later the electrical output current was measured from the first electrode pair. Different sample introduction and measurement delays may be used, depending on the analysis being performed. The measured output current from the first electrode pair was converted into a Hct sample content with a previously determined Hct calibration curve relating output currents to sample Hct contents.

Provided below in Table 13 for blood samples including known 27%, 42%, and 52% Hct (v/v) are analysis-determined Hct contents for one lot of Ag/AgCl working and counter first electrode pair test sensors.

TABLE 13

| Hct | Ave Current | Calculated Hct |
|---|---|---|
| 27% | 187.5 | 26.9 |
| 42% | 143.6 | 42.1 |
| 52% | 106.0 | 54.9 |
| Slope (nA/% Hct) | −288.8 | |
| Int (nA) | 265.3 | |

As can be seen from the table, the analysis-determined Hct content of the samples was substantially representative of the actual Hct sample content. The line slopes obtained also establish the excellent detection sensitivity provided by the active electrode pair equipped test sensors.

A test sensor in accord with FIG. 5 having an inactive carbon working electrode and an active Ag/AgCl counter electrode first electrode pair was used with a measurement device and an amperometric method to determine the Hct content of blood samples. While a test sensor in accord with FIG. 5 was used, a test sensor in accord with FIG. 6 may be used, as both have a first electrode pair.

A blood sample was introduced to the inactive carbon working and active Ag/AgCl counter first electrode pair test sensor at approximately 25° C. After approximately 1-2 second from introduction of the sample to the test sensor, a DC input potential of approximately 2500 mV was applied to the first electrode pair. Approximately 1 second later the electrical output current was measured from the first electrode pair. Different sample introduction and measurement delays may be used, depending on the analysis being performed. The measured output current from the first electrode pair was converted into a Hct sample content with a previously determined Hct calibration curve relating output currents to sample Hct contents.

Provided below in Table 14 for blood samples including known 28%, 42%, and 52% Hct (v/v) are analysis-determined Hct contents for one lot of inactive carbon working and active Ag/AgCl counter electrode pair test sensors.

TABLE 14

| Hct | Ave Current | Calculated Hct |
|---|---|---|
| 28% | 33133 | 23.1% |
| 42% | 24933 | 53.7% |
| 52% | 27233 | 45.1% |
| Slope (nA/% Hct) | −26766 | |
| Int (nA) | 39318 | |

As can be seen from the table, the analysis-determined Hct content of the samples did not correlate as well with the actual Hct sample content of the samples as previously observed with the active electrode pair test sensors. The measured versus actual divergence increased as the Hct content of the sample increased.

However, the observed divergence in these results is believed attributable to the specific test sensor lot used for this analysis. While we are doubtful that an inactive carbon working and active Ag/AgCl counter electrode test sensor could match the detection sensitivity of a similarly configured active electrode pair equipped test sensor, we believe inactive working and active counter electrode pair test sensors could be used to sufficiently determine Hct sample content for many types of analyses.

To provide a clear and more consistent understanding of the specification and claims of this application, the following definitions are provided.

Amperometry is a type of electrochemical sample analysis where current is measured at a substantially constant potential (voltage) as a function of time as a substantially constant potential is applied across the working and counter electrodes of a test sensor. The measured output current, which generally reaches an initial peak and then decays downward, is used to quantify the analyte in the sample. Amperometry measures the rate at which an electrochemically active species is being oxidized or reduced near the working electrode. Many variations of the amperometric method for biosensors have been described, for example in U.S. Pat. Nos. 5,620,579; 5,653,863; 6,153,069; and 6,413,411.

Voltammetry is a type of electrochemical sample analysis that differs from amperometry in that the potential applied across the working and counter electrodes of the test sensor changes continuously with time. The current is measured as a function of the change in the applied potential and/or time to quantify the analyte in the sample. Additional information about voltammetry may be found in "Electrochemical Methods: Fundamentals and Applications" by A. J. Bard and L. R. Faulkner, 1980.

A redox reaction is a reaction between two species involving the transfer of at least one electron from a first species to a second species. Thus, a redox reaction includes an oxidation and a reduction. The oxidation half-cell of the reaction involves the loss of at least one electron by the first species, while the reduction half-cell involves the addition of at least one electron to the second species. The ionic charge of a species that is oxidized is made more positive by an amount equal to the number of electrons removed. Likewise, the ionic charge of a species that is reduced is made less positive by an amount equal to the number of electrons gained. The redox reaction of a species can be either chemical or electrochemical. In an electrochemical redox reaction, an outside charge is applied or removed from a species with an electrode pair.

Oxidation number is the formal ionic charge of a chemical species, such as an atom. A higher oxidation number, such as (III), is more positive, and a lower oxidation number, such as (II), is less positive. A neutral species has an ionic charge of zero. Oxidation of a species results in an increase in the oxidation number of that species, and reduction of a species results in a decrease in the oxidation number of that species.

The physical characteristics of the sample include hematocrit (red blood cell) content, lipid content, protein content, and the like. The physical characteristic of a sample does not relate to a specific molecule (an analyte such as glucose or a ketone) in the sample, but to moieties in the sample that interfere with the charged analyte or charged species responsive to the analyte (such as an electron transfer mediator) diffusing to the working electrode. Thus, the physical characteristic of a sample is determined by how reproducibly the rate at which the charged analyte or charged species responsive to the analyte diffuses to the working electrode for samples having the same analyte concentration.

An analyte specific ionizing agent facilitates the oxidation or reduction of an analyte in the sample. Analyte specific ionizing agents include enzymes such as oxidases, reductases, and dehydrogenases. Unlike an electron transfer mediator, the analyte specific ionizing agent shows a strong preference to the oxidation or reduction of a specific molecular entity or analyte. The analyte specific ionizing agent provides the analyte responsive portion of the electrical output from an electrochemical analysis.

An electron transfer mediator assists in transferring electrons between the analyte or the analyte specific ionizing agent in the sample and the surface of the working electrode. The electron transfer mediator is a reagent in the electrochemical analysis of the sample and is not the analyte of interest, but provides for the indirect measurement of the analyte. The mediator also assists in maintaining the oxidation state of the analyte specific ionizing agent. Mediators undergo reversible redox reactions during the analysis and are not the analyte of interest, but provide for the indirect measurement of the analyte. Thus, the mediator undergoes a redox reaction in response to the oxidation or reduction of the analyte and becomes a charged species responsive to the analyte. The oxidized or reduced mediator then undergoes the opposite reaction at the working electrode and is regenerated to its original oxidation number. Mediators that may undergo oxidation during the analysis include ferrocyanides, p-hydroquinone and its derivatives, reduced phenazines methosulfate, leucomethylene blue, ruthenium (II) hexaamine, ferrocene, and ferrocene derivatives. Mediators that may undergo reduction during the analysis include ferricyanides, p-benzoquinone, p-benzoquinone and its derivatives, oxidized phenazines methosulfate, methylene blue, ruthenium (III) hexaamine, ferricinium, and ferricinium derivatives. Mediators that may transfer more than one electron at substantially the same time during the analysis include 3-phenylimino-3H-phenothiazines, 3-phenylimino-3H-phenoxazines, salts thereof, acids thereof, and derivatives thereof. Mediators are not elemental metals.

An electrode pair refers to a working electrode and a counter electrode. When an electric potential is applied to the electrode pair by a measurement device, current flows between the working and counter electrodes by passing through the sample.

A working electrode is where one or more species undergo electrochemical redox reaction.

A counter electrode is where the opposite of the electrochemical redox reaction ongoing at the working electrode occurs, thus allowing current to flow between the working and counter electrodes. For example, if an analyte undergoes oxidation at the working electrode, reduction occurs at the counter electrode. See, for example, Fundamentals Of Analytical Chemistry, $4^{th}$ Edition, D. A. Skoog and D. M. West; Philadelphia: Saunders College Publishing (1982), pp 304-341.

An active electrode includes at least one material that changes its oxidation state during the analysis. Thus, at least one element of the electrode core material loses or acquires electrons during the analysis and directly participates in the electrochemical reaction of the sample. The element that changes its oxidation state during the analysis may be an ionized metal in the form of a salt or the like when the material is deposited on the electrical conductor/s of the test sensor to form the electrode core. An example would be silver-silver chloride (Ag/AgCl) and the like. The element that changes its oxidation state during the analysis also may be a non-ionized metal when the material is deposited on the electrical conductor/s of the test sensor to form the electrode core. In this instance of a non-ionized metal, the metal is reduced or oxidized at the potential and duration of the analysis. An example would be silver metal.

An inactive electrode lacks a material exposed to the sample that can change its oxidation state and participate in the electrochemical reaction of the sample during the analysis. Thus, the elements of the electrode exposed to the sample during the analysis do not lose or acquire electrons (ionize) during the analysis and do not participate in the electrochemical oxidation or reduction of the sample. Inactive elements include carbon, palladium, gold, titanium, and platinum. An inactive electrode may be formed from an active electrode by coating the otherwise active electrode with an inactive coating isolating the element that could undergo oxidation or reduction during the analysis from the sample. Inactive coatings may be inactive elements, ceramics, polymers, and the like. Examples of inactive polymeric coatings include carboxymethyl cellulose, hydroxyethyl cellulose, hydroxypropyl cellulose, methyl cellulose, ethyl cellulose, ethylhydroxyethyl cellulose, carboxymethyl cellulose, polyvinyl alcohol, polyvinyl pyrrolidone, polyamino acids, polystyrene sulfonate, polyacrylic acid, polymethacrylic acid, starch, polymerized maleic anhydride, and agarose gels.

A polymeric binder is a material that provides physical support and containment to the reagents while having chemical compatibility with the reagents. Polymeric binders do not chemically react or electrochemically participate in the analysis of the sample.

Hematocrit bias refers to the difference between the reference glucose concentration obtained with a reference instrument uninfluenced by the red blood cell content of the blood sample and a hematocrit-influenced experimental glucose reading obtained from the measurement device of a biosensor system for samples containing differing hematocrit levels. The difference between the reference and values obtained from the biosensor results from the varying hematocrit levels between specific whole blood samples. The difference between the reference and values obtained from the system results from the varying hematocrit level between specific whole blood samples and may be generally expressed as a percentage by the following equation: % Hct–Bias=$100\% \times (G_d - G_{ref})/G_{ref}$, where $G_d$ and $G_{ref}$ are the determined glucose and reference glucose concentration readings, respectively, for any hematocrit level. The larger the absolute value of the % Hct–bias, the more the hematocrit level of the sample (expressed as % Hct: the percentage of red blood cell volume/sample volume) is reducing the accuracy of the determined glucose concentration. For example, if whole blood samples containing identical glucose concentrations, but having hematocrit levels of 20, 40, and 60%, are analyzed, three different glucose readings will be reported by a system based on one set of calibration constants (slope and intercept of the 40% hematocrit containing whole blood sample, for instance). Hematocrit sensitivity refers to the degree to which changes in the hematocrit level of a sample affect the bias values for an analysis.

The term "on" is defined as "above" and is relative to the orientation being described. For example, if a first element is deposited over at least a portion of a second element, the first element is said to be "deposited on" the second. In another example, if a first element is present above at least a portion of a second element, the first element is said to be "on" the second. The use of the term "on" does not exclude the presence of substances between the upper and lower elements being described. For example, a first element may have a coating over its top surface, yet a second element over at least a portion of the first element and its top coating can be described as "on" the first element. Thus, the use of the term "on" may or may not mean that the two elements being related are in physical contact with each other. The use of the term "on" does not exclude when a portion of a second layer deposited on a first layer partially penetrates the first layer.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A test sensor for determining a corrected analyte concentration of a sample comprising:
   a substrate;
   at least two electrical conductor contacts and at least two electrical conductors, each electrical conductor contact in electrical communication with an electrical conductor, where the electrical conductor contacts are on the substrate;

a lid on the substrate forming a sample reservoir with the substrate, the sample reservoir comprising an inlet port; and at least two pair of electrodes in the sample reservoir in electrical communication with the electrical conductors, where a first electrode pair in the sample reservoir includes an active counter electrode, the active counter electrode comprising a core material configured to change oxidation state and directly participate during an electrochemical analysis of a sample, and a second electrode pair in the sample reservoir includes an analyte specific ionizing agent on a working electrode of the second electrode pair.

2. The test sensor of claim 1, the first electrode pair lacking an electron transfer mediator on either electrode of the first electrode pair.

3. The test sensor of claim 1, the first electrode pair lacking the analyte specific ionizing agent on either electrode of the first electrode pair.

4. The test sensor of claim 1, the active counter electrode comprising an electrode core consisting essentially of a substantially homogenous core material.

5. The test sensor of claim 1, the active counter electrode comprising an electrode core material selected from the group consisting of silver and silver chloride salt (Ag/AgCl) and silver metal and carbon (AgC).

6. The test sensor of claim 1, the first electrode pair further comprising an active working electrode.

7. The test sensor of claim 6, the active working electrode comprising an electrode core consisting essentially of a substantially homogenous core material.

8. The test sensor of claim 6, the active counter electrode and the active working electrode comprising an electrode core material including silver and silver chloride salt (Ag/AgCl).

9. The test sensor of claim 8, the electrode core material including from 70% to 90% (weight/weight) silver.

10. The test sensor of claim 6, the active counter electrode and the active working electrode comprising an electrode core material including a mixture of silver metal and carbon (AgC).

11. The test sensor of claim 10, the electrode core material including from 20% to 60% (weight/weight) silver metal and non-silver metal core material, where the non-silver metal core material is at least 90% (weight/weight) carbon.

12. The test sensor of claim 1, the second electrode pair further comprising an electron transfer mediator on the working electrode of the second electrode pair.

13. The test sensor of claim 1 where the first electrode pair is in closer proximity to the inlet port than the second electrode pair.

14. The test sensor of claim 1 where the first electrode pair is located in a first reservoir branch of the sample reservoir and the second electrode pair is located in a second branch of the sample reservoir.

15. A test sensor for determining a physical characteristic of a sample, comprising:

a substrate;

two electrical conductor contacts and two electrical conductors, each electrical conductor contact in electrical communication with an electrical conductor, where the electrical conductor contacts are on the substrate;

a lid on the substrate forming a sample reservoir with the substrate, the sample reservoir comprising an inlet port; and one pair of electrodes in the sample reservoir and in electrical communication with the electrical conductors, where the one pair of electrodes in the sample reservoir includes an active counter electrode, the active counter electrode comprising a core material configured to change oxidation state and directly participate during an electrochemical physical characteristic analysis of a sample, and where the active counter electrode comprising an electrode core consisting essentially of a substantially homogenous core material.

16. The test sensor of claim 15, the one electrode pair lacking an electron transfer mediator on either electrode of the one electrode pair.

17. The test sensor of claim 15, the one electrode pair lacking an analyte specific ionizing agent on either electrode of the one electrode pair.

18. The test sensor of claim 15, the active counter electrode comprising an electrode core material selected from the group consisting of silver and silver chloride salt (Ag/AgCl) and silver metal and carbon (AgC).

19. The test sensor of claim 15, the one electrode pair further comprising an active working electrode.

20. The test sensor of claim 19, the active working electrode comprising an electrode core consisting essentially of a substantially homogenous core material.

21. The test sensor of claim 19, the active counter electrode and the active working electrode comprising an electrode core material including silver and silver chloride salt (Ag/AgCl).

22. The test sensor of claim 21, the electrode core material including from 70% to 90% (weight/weight) silver.

23. The test sensor of claim 19, the active counter electrode and the active working electrode comprising an electrode core material including a mixture of silver metal and carbon (AgC).

24. The test sensor of claim 23, the electrode core material including from 20% to 60% (weight/weight) silver metal and non-silver metal core material, where the non-silver metal core material is at least 90% (weight/weight) carbon.

25. The test sensor of claim 19, where the sample inlet is centrally located over the working electrode.

26. A system for determining a corrected analyte concentration of a sample comprising:

a measurement device having contacts in electrical communication with electrical conductor contacts of a test sensor, each electrical conductor contact in electrical communication with an electrical conductor, where the electrical conductor contacts are on a substrate of the test sensor, the measurement device includes contacts in electrical communication with circuitry including a processor in electrical communication with an electrical input generator and with a storage medium, the test sensor includes a lid on the substrate forming a sample reservoir with the substrate, the sample reservoir comprising an inlet port, the test sensor includes at least two pair of electrodes in the sample reservoir in electrical communication with the electrical conductors of the test sensor, where a first electrode pair in the sample reservoir includes an active counter electrode, and a second electrode pair in the sample reservoir includes an analyte specific ionizing agent on a working electrode of the second electrode pair;

the electrical input generator is configured to apply an electrical input of at least 400 mV to the contacts of the measurement device in response to an instruction from the processor;

the test sensor is configured to generate an electrical output from the second electrode pair responsive to an analyte concentration of a sample, the sample in electrical communication with the second electrode pair;

the test sensor is configured to generate an electrical output from the first electrode pair responsive to a physical characteristic of the sample, the sample in electrical communication with the first electrode pair, the first electrode pair including an active counter electrode, the active counter electrode comprising a core material configured to change oxidation state and directly participate during an electrochemical analysis of a sample when the electrical input of at least 400 mV is applied to the contacts of the measurement device;

the processor is configured to correct the electrical output from the second electrode pair with the electrical output from the first electrode pair in response to non-transient instructions stored in the storage medium; and the processor is configured to determine a corrected analyte concentration of the sample in response to non-transient instructions stored in the storage medium.

27. The system of claim 26, where the electrical input is direct current, where the direct current is continuous or multiple pulses.

28. The system of claim 26, where the measurement device further comprises a display in electrical communication with the processor, the processor configured to provide the corrected analyte concentration of the sample to the display.

29. The system of claim 26, the first electrode pair lacking an electron transfer mediator on either electrode of the first electrode pair.

30. The system of claim 26, the first electrode pair lacking the analyte specific ionizing agent on either electrode of the first electrode pair.

31. The system of claim 26, the test sensor configured where the electrical output generated from the second electrode pair is responsive to a redox reaction of the analyte with an analyte specific ionizing agent.

32. The system of claim 31, the test sensor configured where the electrical output generated from the second electrode pair is responsive to a redox reaction of the analyte specific ionizing agent with an electron transfer mediator.

33. The system of claim 31, the active working electrode comprising an electrode core consisting essentially of a substantially homogenous core material.

34. The system of claim 31, the active counter electrode and the active working electrode comprising an electrode core material including silver and silver chloride salt (Ag/AgCl).

35. The system of claim 34, the electrode core material including from 70% to 90% (weight/weight) silver.

36. The system of claim 31, the active counter electrode and the active working electrode comprising an electrode core material including a mixture of silver metal and carbon (AgC).

37. The system of claim 36, the electrode core material including from 20% to 60% (weight/weight) silver metal and non-silver metal core material, where the non-silver metal core material is at least 90% (weight/weight) carbon.

38. The system of claim 26, the test sensor configured where the electrical output from the first electrode pair is substantially not responsive to the analyte concentration of the sample.

39. The system of claim 26, where the first electrode pair of the test sensor is configured to generate a useful hematocrit response to be read by the processor.

40. The system of claim 26, where the first electrode pair of the test sensor is configured to generate a useful detection sensitivity to be read by the processor.

41. The system of claim 26, where the electrical input generator is configured to apply an electrical input from 1,000 mV to 10,000 mV to the contacts of the measurement device in response to an instruction from the processor.

42. The system of claim 26, where the electrical input generator is configured to apply an electrical input from 2,000 mV to 6,000 mV to the contacts of the measurement device in response to an instruction from the processor.

43. The system of claim 26, where the correction configuration of the processor includes:

the processor configured to determine an uncorrected analyte concentration of the sample and a physical characteristic content of the sample with previously prepared non-transient calibration curves stored in the storage medium, the previously prepared calibration curves including:

a relationship between analyte responsive generated output from the second electrode pair and analyte concentration of the sample, and a relationship between physical characteristic generated output from the first electrode pair and physical characteristic content of the sample; and the processor configured to correct the uncorrected analyte concentration of the sample with the physical characteristic content of the sample.

44. The system of claim 26, where the determination configuration of the processor includes the processor configured to transform a corrected electrical output with a previously prepared non-transient calibration curve stored in the storage medium, the previously prepared non-transient calibration curve including a non-transient relationship between the corrected electrical output and the corrected analyte concentration of the sample.

45. The system of claim 26, the active counter electrode comprising an electrode core consisting essentially of a substantially homogenous core material.

46. The system of claim 26, the active counter electrode comprising an electrode core material selected from the group consisting of silver and silver chloride salt (Ag/AgCl) and silver metal and carbon (AgC).

47. The system of claim 26, the first electrode pair further comprising an active working electrode.

48. The system of claim 26, the second electrode pair further comprising an electron transfer mediator on the working electrode of the second electrode pair.

49. The system of claim 26 where the first electrode pair is in closer proximity to the inlet port than the second electrode pair.

50. The system of claim 26 where the first electrode pair is located in a first reservoir branch of the sample reservoir and the second electrode pair is located in a second branch of the sample reservoir.

51. A system for determining a physical characteristic of a sample, comprising:

a measurement device having contacts in electrical communication with electrical conductor contacts of a test sensor, each electrical conductor contact in electrical communication with an electrical conductor, where the electrical conductor contacts are on a substrate of the test sensor, the measurement device includes contacts in electrical communication with circuitry including a processor in electrical communication with an electrical input generator and with a storage medium, the test sensor includes a lid on the substrate forming a sample reservoir with the substrate, the sample reservoir comprising an inlet port, the test sensor includes one pair of electrodes in the sample reservoir in electrical communication with the electrical conductors of the test sensor, where the one pair of electrodes in the sample reservoir include an active counter electrode, and the electrical input generator is configured to apply an electrical input from 2,000 mV to 6,000 mV to the contacts of the measurement device in response to an instruction from the processor;

the test sensor is configured to generate an electrical output from one electrode pair on the substrate responsive to a physical characteristic of the sample, the sample in electrical communication with the one electrode pair, the one electrode pair including an active counter electrode, the active counter electrode comprising a core material configured to change oxidation state and directly participate during an electrochemical analysis of a sample when the electrical input from 2,000 mV to 6,000 mV is applied to the contacts of the measurement device;

the processor is configured to determine a physical characteristic content of the sample in response to non-transient instructions stored in the storage medium.

52. The system of claim 51, where the electrical input is direct current, where the direct current is continuous or multiple pulses.

53. The system of claim 51, where the measurement device further comprises a display in electrical communication with the processor, the processor configured to provide the physical characteristic content of the sample to the display.

54. The system of claim 51, the one electrode pair lacking an electron transfer mediator on either electrode of the one electrode pair.

55. The system of claim 51, the one electrode pair lacking an analyte specific ionizing agent on either electrode of the one electrode pair.

56. The system of claim 51, the active counter electrode comprising an electrode core consisting essentially of a substantially homogenous core material.

57. The system of claim 51, the test sensor configured where the electrical output from the one electrode pair is substantially not responsive to an analyte concentration of the sample.

58. The system of claim 51, where the physical characteristic of the sample is selected from the group consisting of hematocrit content of the sample, viscosity of the sample, and combinations thereof.

59. The system of claim 51, where the sample is blood and the physical characteristic of the sample is a hematocrit content of the blood.

60. The system of claim 51, where the one electrode pair of the test sensor is configured to generate a useful hematocrit response to be read by the processor.

61. The system of claim 51, where the one electrode pair of the test sensor is configured to generate a useful detection sensitivity to be read by the processor.

62. The system of claim 51, where the determination configuration of the processor includes the processor configured to transform the electrical output from the one electrode pair into the physical characteristic content of the sample with a previously prepared non-transient calibration curve stored in the storage medium, the previously prepared non-transient calibration curve including a non-transient relationship between physical characteristic generated output from the one electrode pair and the physical characteristic content of the sample.

63. The system of claim 51, the active counter electrode comprising an electrode core material selected from the group consisting of silver and silver chloride salt (Ag/AgCl) and silver metal and carbon (AgC).

64. The system of claim 51, the one electrode pair further comprising an active working electrode.

65. The system of claim 64, the active working electrode comprising an electrode core consisting essentially of a substantially homogenous core material.

66. The system of claim 64, the active counter electrode and the active working electrode comprising an electrode core material including silver and silver chloride salt (Ag/AgCl).

67. The system of claim 66, the electrode core material including from 70% to 90% (weight/weight) silver.

68. The system of claim 51, the active counter electrode and the active working electrode comprising an electrode core material including a mixture of silver metal and carbon (AgC).

69. The system of claim 68, the electrode core material including from 20% to 60% (weight/weight) silver metal and non-silver metal core material, where the non-silver metal core material is at least 90% (weight/weight) carbon.

70. An active electrode pair for participating in the electrochemical reaction of an analyte in a sample, the active electrode pair comprising:
a working electrode conductor;
a working electrode core on the working electrode conductor, the working electrode core consisting essentially of carbon, silver metal, silver chloride, and combinations thereof;
a counter electrode conductor; and
a counter electrode core on the counter electrode conductor, the counter electrode core consisting essentially of carbon and silver metal, silver metal and silver chloride, and combinations thereof, where the silver content of the counter electrode is from 70% to 90% (weight/weight).

71. The active electrode pair of claim 70, where the working electrode core and the counter electrode core are substantially homogenous.

72. The active electrode pair of claim 70, where the silver content of the counter electrode is from 75% to 85% (weight/weight).

73. The active electrode pair of claim 70, where the silver content of the working electrode is from 70% to 90% (weight/weight).

* * * * *